(12) United States Patent
Gavardinas et al.

(10) Patent No.: US 7,807,691 B2
(45) Date of Patent: Oct. 5, 2010

(54) SUBSTITUTED N-ARYLPYRROLIDINES AS SELECTIVE ANDROGEN RECEPTOR MODULATORS

(75) Inventors: Konstantinos Gavardinas, Monrovia, IN (US); Prabhakar Kondaji Jadhav, Zionsville, IN (US); Douglas Richard Stack, Fishers, IN (US)

(73) Assignee: Eli Lilly and Company, Indianapolis, IN (US)

(*) Notice: Subject to any disclaimer, the term of this patent is extended or adjusted under 35 U.S.C. 154(b) by 160 days.

(21) Appl. No.: 11/913,710

(22) PCT Filed: May 10, 2006

(86) PCT No.: PCT/US2006/018061
§ 371 (c)(1),
(2), (4) Date: Nov. 6, 2007

(87) PCT Pub. No.: WO2006/124447
PCT Pub. Date: Nov. 23, 2006

(65) Prior Publication Data
US 2008/0176864 A1 Jul. 24, 2008

Related U.S. Application Data

(60) Provisional application No. 60/680,911, filed on May 13, 2005.

(51) Int. Cl.
A61K 31/4025 (2006.01)
C07D 207/06 (2006.01)
C07D 207/08 (2006.01)
C07D 207/10 (2006.01)

(52) U.S. Cl. ...................... 514/303; 548/577

(58) Field of Classification Search .............. 548/577; 514/303
See application file for complete search history.

(56) References Cited

U.S. PATENT DOCUMENTS 5,411,981 A    5/1995  Gaillard-Kelly et al.
2004/0157859 A1*  8/2004  Wu et al. ............... 514/255.05

FOREIGN PATENT DOCUMENTS

WO   WO 01/27107 A2    4/2001
WO   WO 2004/016576 A1  2/2004
WO   WO 2005/000795    1/2005

OTHER PUBLICATIONS

RN 860759-80-4, retrieved from CAPLUS on Jun. 10, 2009.*
Tucker, et al., "Nonsteroidal Antiandrogens. Synthesis and Structure-Activity Relationships of 3-Substituted Derivatives of 2-Hydroxypropionanilides," *Journal of Medicinal Chemistry*, American Chemical Society. Washington, US, vol. 31, No. 5, pp. 954-959 (1988).
Elslager, et al., "Folate Antagonists. 3. 2,4-Diamino-6-(Heterocyclic)Quinazolines, a Novel Class of Antimetabolites with Potent Antimalarial and Antibacterial Activity," *Journal of Medicinal Chemistry*, American Chemical Society. Washington, US, vol. 15, No. 8, pp. 827-836 (1972).

* cited by examiner

Primary Examiner—Rebecca L Anderson
Assistant Examiner—Shawquia Young
(74) Attorney, Agent, or Firm—Alexander Wilson

(57) ABSTRACT

The present invention provides a compound of the Formula (I) or a pharmaceutically acceptable salt thereof; pharmaceutical compositions comprising an effective amount of a compound of Formula (I) in combination with a suitable carrier, diluent, or excipient; and methods for treating physiological disorders, particularly frailty, osteoporosis, osteopenia, and male and female sexual dysfunction comprising administering to a patient in need thereof an effective amount of a compound of Formula (I).

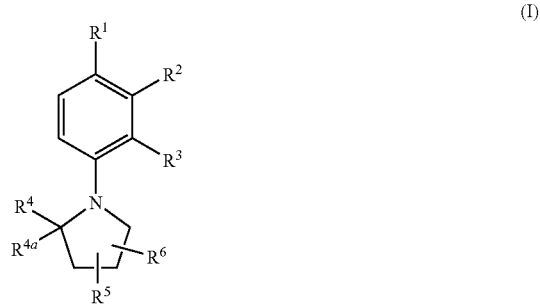

15 Claims, No Drawings

SEQUENCE LISTING

<160> NUMBER OF SEQ ID NOS: 3

<210> SEQ ID NO 1
<211> LENGTH: 15
<212> TYPE: DNA
<213> ORGANISM: Artificial
<220> FEATURE:
<223> OTHER INFORMATION: Synthetic Construct

<400> SEQUENCE: 1

```
ggttcttgga gtact                                                    15

<210> SEQ ID NO 2
<211> LENGTH: 15
<212> TYPE: DNA
<213> ORGANISM: Artificial
<220> FEATURE:
<223> OTHER INFORMATION: Synthetic Construct

<400> SEQUENCE: 2
tgtacaggat gttct                                                    15

<210> SEQ ID NO 3
<211> LENGTH: 15
<212> TYPE: DNA
<213> ORGANISM: Artificial
<220> FEATURE:
<223> OTHER INFORMATION: Synthetic Construct

<400> SEQUENCE: 3
tgtacaggat gttct                                                    15
```

US 7,807,691 B2

SUBSTITUTED N-ARYLPYRROLIDINES AS SELECTIVE ANDROGEN RECEPTOR MODULATORS

This application is a national stage application under 35 U.S.C. §371 of PCT/US06/18061 filed on May 10, 2006 which claims benefit of U.S. Provisional Application No. 60/680,911 filed on May 13, 2005.

TECHNICAL FIELD OF INVENTION

The present invention relates to substituted N-arylpyrrolidine compounds that are useful as therapeutic agents, to pharmaceutical compositions comprising the compounds, to methods of using the compounds to treat disorders in patients, and to intermediates and processes useful in the synthesis of the compounds.

BACKGROUND OF THE INVENTION

Nuclear hormone receptors are an evolutionarily conserved class of intracellular receptor proteins which have been termed "ligand dependent transcription factors". Evans et al., SCIENCE, 240: 889 (1988). The nuclear hormone receptor gene superfamily encodes structurally-related receptor proteins for glucocorticoids (e.g. cortisol, corticosterone, cortisone), androgens, mineralocorticoids (e.g. aldosterone), progestins, estrogen, and thyroid hormone. Also included within this superfamily of nuclear receptors are receptor proteins for vitamin D, retinoic acid, 9-cis retinoic acid, as well as those receptors for which no cognate ligands have been identified ("orphan receptors") Ribeiro et al., Annual Rev. Med., 46:443-453 (1995); Nature Rev. Drug Discovery, 3: 950-964 (November 2004). Steroid hormone receptors represent a subset of the nuclear hormone receptor superfamily. So named according to the cognate ligand which complexes with the receptor in its native state, the steroid hormone nuclear receptors include the glucocorticoid receptor (GR), the androgen receptor (AR), the mineralocorticoid receptor (MR), the estrogen receptor (ER), and the progesterone receptor (PR). Tenbaum et al., Int. J. Biochem. Cell. Bio., 29(12):1325-1341 (1997).

In contrast to membrane bound receptors, nuclear hormone receptors encounter their respective ligands following entry of the ligand into the cell. Once ligand binding occurs, the ligand-receptor complex modulates transcription of target genes within the cell nucleus. For example, most ligand-free nuclear receptors are bound in a complex with heat shock proteins (hsps) in the cytoplasm. Following entry of circulating hormone into the cell, binding elicits a conformational change in the receptor, dissociating the receptor from the hsp. The ligand bound receptors translocate to the nucleus, where they act as monomers as well as hetero- and homodimers in binding to particular hormone response elements (HREs) in the promoter regions of target genes. The HRE-receptor complex then, in turn, regulates transcription of proximally-located genes. (see Ribeiro et al., supra.). On the other hand, thyroid hormone receptors (TRs) and other non-steroid receptors such as vitamin D receptor (VDR) and retinoic acid receptors (RAR) are bound to their respective HRE in the absence of hsps and/or cognate ligand. Hormones released from the circulation enter the cell, binding in the nucleus to these receptors which, in turn, hetero-dimerize to other nuclear receptors such as 9-cis retinoic acid (RXR). As with the steroid hormone nuclear receptors, following ligand binding, the ligand-bound receptor complex again regulates transcription of neighboring genes.

Androgens exert profound influences on a multitude of physiological functions by virtue of their diverse roles in inter alia male sexual development and function, maintenance of muscle mass and strength in both males and females, maintenance of bone mass, erythropoeisis, memory and cognition, and maintenance of sexual behaviour (e.g. libido and potency). The actions of androgens (testosterone and 5α-dihydrotestosterone (DHT)) are mediated by the AR which, upon androgen binding, translocates to the cell nucleus where it binds to specific DNA sequences termed androgen response elements (AREs) to initiate or repress transcription of target genes. The effects of androgens can be generally characterized as anabolic or androgenic in nature. Anabolic (i.e. tissue building) effects of androgens include increasing muscle mass and strength and bone mass, whereas androgenic (i.e. masculinizing) effects include the development of male secondary sexual characteristics such as the internal reproductive tissues (i.e. prostate and seminal vesicle), the external genitalia (penis and scrotum), libido, and hair growth patterns.

Reductions in bioavailable serum androgen levels that occur with aging can have serious physiological effects in both males and females. In males, for example, decreases in androgen levels are associated with loss of libido, erectile dysfunction, depression, decreased cognitive ability, lethargy, osteoporosis, and loss of muscle mass and strength. Rajfer (2003), *Rev. Urol.,* 5 (Suppl. 1): S1-S2. In addition, as men age and testosterone levels decline, bones weaken, diabetes and cardiovascular disease rates increase, and the ratio of muscle mass to fat decreases. Vastag, B. (2003), *JAMA;* 289: 971-972. In females, low plasma levels of circulating testosterone are associated with diminished libido, unexplained fatigue, and general lack of well being. Davis, S. R. (1999), *Medical J. Australia;* 170: 545-549. Clinically, the principal application of androgen therapy has been in the treatment of hypogonadism in men. Significantly, androgen replacement therapy in hypogonadal men has also been shown to decrease bone resorption and increase bone mass. Katznelon, L., et al., *J. Clin. Enidocrinol Metab.;* 81: 4358 (1996). Other indications for which androgens have been used clinically include treatment of delayed puberty in boys, anemia, primary osteoporosis, and muscle wasting diseases. In addition, androgen replacement therapy has been used recently in aging men and for the regulation of male fertility. T. R. Brown, *Endocrinology;* 145(12): 5417-5419 (2004). In females, androgen therapy has been used clinically for the treatment of sexual dysfunction or diminished libido. W. Arlt, *Euro. J. Endocrinol.;* 154(1) 1-11 (2006).

However, activation of AR in certain tissues is also associated with serious deleterious consequences. For example, unwanted side effects of steroidal androgen therapy include growth stimulation of the prostate and seminal vesicles. Feldkorn et al., *J. Steroid Bichem and Mol. Biol.;* 94(5): 481-487 (2005). Prostate cancers, for example, depend on AR for growth and development. Gegory, C. W. et al. (2001), *Cancer Res.,* June 1; 61(11):4315-4319; and Jenster, G. (1999), *Semin. Oncol.,* August; 26(4): 407-421. Androgen therapy has also been associated with sleep apnea, stimulation of prostate tumors and elevations in prostate specific antigen (PSA), an indication of increased prostate cancer risk. Vastag, B. (2003), *JAMA;* 289: 971-972. In addition, use of androgen agonists have specifically been associated with liver damage, adverse effects on male sexual function, adverse effects associated with cardiovascular and erythropoetic function, prostate enlargement, hisutism, and virilization. (see Published International Patent Applications WO 03/011824 and WO 03/034987) Furthermore, preparations of unmodified and modified steroidal androgens have been found to suffer from rapid degradation in the liver leading to poor oral bioavailability and short duration of activity following parenteral administration, variations in plasma levels, hepatotoxicity, or cross reactivity with other steroid hormone receptors (e.g. the glucocorticoid receptor (GR), the mineralocorticoid receptor (MR), and the progesterone receptor (PR) which have ligand binding domains homologous to AR) Yin et al., *JPET;* 304(3): 1323-1333 (2003). Furthermore, in females, the use of steroidal androgens may lead to hirsutism or virilization.

Thus, there remains a need in the art for alternatives to classical steroidal androgen therapy which possess the beneficial pharmacological properties of steroidal androgens, but with a reduced likelihood or incidence of the typical limitations associated with steroidal androgen therapy. Recent efforts to identify suitable replacements for steroidal androgens have focused on identifying tissue selective androgen receptor modulators (SARMs) which display a differentiated profile of activity in androgenic tissues. In particular, such agents preferably display androgen agonist activity in anabolic tissues such as muscle or bone, yet are only partial agonists or even antagonists in androgenic tissues such as the prostate or seminal vesicles.

Ligands used to modulate (i.e., agonize, partially agonize, partially antagonize, or antagonize) the transcriptional activity of AR display androgenic or antiandrogenic activity (or anabolic or antianabolic activity) and, further, may be steroidal or nonsteroidal in structure. Androgenic agents (AR Agonists or partial AR agonists) mimic the effects of natural androgens in either activating or repressing the transcriptional activity of AR, whereas antiandrogenic agents (AR antagonists or partial AR antagonists) block androgen mediated transactivation or transrepression of AR. Further, the AR ligand-AR complex has also been reported to influence the recruitment of cofactor proteins to the enhancer and or promoter sites. Shang et al. (March 2002), *Mol. Cell.* 9(3): 601-610. In addition to their effects on target gene transcription, ligands for AR may also induce "non-genotropic" effects. For example, ligands can bind to AR localized in non-nuclear compartments such as the endoplasmic reticulum, outer cell membrane, or cytoplasm and induce biochemical changes that are mediated by adaptor proteins such as phosphatidylinositol-3-kinase (PI3K), extracellular regulated kinases (ERKs), mitogen activated protein kinases (MAPKs), or p38/stress activated protein kinase/c-Jun N-terminal kinases (p38/SAP/JNK). These "non-genotropic" effects encompass a wide array of physiological changes such including the triggering of antiapoptotic and survival pathways. (see Bowen, R. L. (2001), *JAMA* 286(7): 790-1; Gouras, G. K., H. Xu, et al. (2000), *Proc. Natl. Acad. Sci. USA* 97(3): 1202-5; Kousteni, S., T. Bellido, et al. (2001), *Cell* 104(5): 719-30; and Kousteni, S., L. Han, et al. (2003) [comment] *Journal of Clinical Investigation* 111(11): 1651-64.)

Thus, it is clear that a ligand which has affinity for AR could be used to modulate receptor activity and thereby influence a multitude of physiological effects related to alterations in androgen levels and/or AR activity. Furthermore, the effects of such agents can be accomplished by both classical conventional HRE-mediated (e.g. "genotropic") or non-genotropic mechanisms. Preferably such agents function as selective androgen receptor modulators (SARMs) displaying androgenic effects in tissues such as muscle and/or bone, while concomitantly displaying antiandrogenic properties in tissues such as the prostate, liver, and those responsible for virilization in females. Alternatively, SARMs may display tissue selectivity with regard to their androgenic effects functioning as, for example, agonists in anabolic tissue such as muscle or bone but only partial agonists or antagonists in tissues such as the prostate or seminal vesicles. In addition, such ligands are preferably non-steroidal in nature thus avoiding many of the undesired pharmacological, physiochemical and pharmacokinetic properties of their steroidal counterparts, including poor oral bioavailability, rapid hepatic metabolism, and cross activation of other steroid receptors. He, Y, et al. (2002), *Eur. J. Med. Chem.;* 37: 619-634.

Several physiological disorders are believed to be susceptible to AR modulation, and in particular, modulation by SARMs. Frailty represents one such disorder. Frailty is a geriatric condition which results in a reduction in one's reserve capacity to the extent that multiple physiological systems are close to, or past the threshold of symptomatic clinical failure. As a consequence, the frail person is at an increased risk of disability and death from minor external stresses (e.g. disease or life events). Campbell, A. J., et al. (1997), Age and Ageing; 26(4): 315-318. Frailty represents a complex syndrome characterized by numerous musculoskeletal symptoms including declines in muscle mass and strength, decreased range of motion, slowness and paucity of movement, balance and gait abnormalities, weight loss and reduced food intake, weakness and fatigue, decreased exercise tolerance, and sarcopenia (loss of lean body mass). Brown, M., et al. (2000), *J. of Gerontology;* 55(6): M350-M355; and Fried, L. and Watson, J. (1999), *Principles of Geriatric Medicine and Gerontolgy,* 1387-1402, New York: McGraw Hill. As such, an agent with androgenic properties in tissues such as muscle and bone would be expected to have utility in treating the frail patient.

Other physiological disorders are also suitable for AR modulation. For example, it is now well known that hypogonadism is associated with osteoporosis in men. Kaufman, J. M., et al., *Ann. Rheum. Dis.;* October; 59(10): 765-772 (2000). Furthermore, in men with prostate cancer, androgen deprivation therapy increased the rate of bone mineral density loss. Preston, D. M., et al., *Prostate Cancer Prostatic Dis.;* 5(4): 304-310 (2002). In addition, androgen replacement therapy in hypogonadal men decreases bone resorption and increases bone mass. Katznelon, L., et al., *J. Clin. Endocrinol Metab.;* 81: 4358 (1996). As such, AR modulators are believed to be useful in the treatment of osteoporosis (either as a monotherapy or in combination with other inhibitors of bone resorption including, but not limited to estrogens, bisphosphonates, and selective estrogen receptor modulators). In fact, small clinical trials have in fact shown that testosterone replacement therapy in older men may help delay or reverse osteoporosis, possibly preventing hip and vertebral fractures. Vastag, B., *JAMA;* 289: 971-972 (2003).

Moreover, AR modulators, can be used to enhance performance in the treatment of male and female sexual dysfunction (see Morley, J. E. and Perry, H. M., *J. Steroid Biochem. Mol. Biol.;* June; 85(2-5): 367-373 (2003) and *Medical J. Australia;* 170: 545-549 (1999), supra). Other indications or physiological disorders or for which an AR modulator is believed to have utility include maintenance of muscle mass, strength and function; as bone anabolic agents in the treatment of osteoporosis or osteopenia; restoration of bone either independently or as an adjunct to androgen deprivation therapy in the treatment of prostate or pancreatic cancer; as an agent to accelerate bone repair (e.g. bone fractures); as a treatment for sarcopenia or Age Related Functional Decline (ARFD); as an agent to increase energy (e.g. reduce lethargy) and libido; or as a treatment for hypogonadism. In addition, AR modulators can be used for the treatment of prostate cancer.

Thus, it is an object of the present invention to provide nonsteroidal AR ligands which possess androgen receptor modulating activity. In particular, it is an object of the present invention to provide nonsteroidal AR ligands which possess androgen receptor agonist activity. More particularly, it is a preferred embodiment of the present invention to provide nonsteroidal androgen agonists which bind to AR with greater affinity relative to the other steroid hormone receptors. Even more particularly, it is a preferred embodiment of the present invention to provide tissue selective androgen receptor modulators (SARMs) which display androgen agonist activity in muscle or bone, but only partial agonist, partial antagonist or antagonist activity in other androgenic tissues such as the prostate or seminal vesicle.

The following references describe examples of the state of the art as it relates to the present invention.

He et al., Eur. J. Med. Chem.; 37: 619-634 (2002) discloses bicalutamide analogs as nonsteroidal Androgen receptor ligands.

Published International PCT Application WO 03/011302 A1 discloses androstene derivative compounds as androgen receptor modulators.

Published International PCT Application WO 03/077919 A1 discloses azasteroid derivative compounds as androgen receptor modulators.

Published International PCT Application WO 02/16310 A1 discloses bicalutamide analogs as nonsteroidal Androgen receptor ligands.

Published International PCT Application WO 03/034987 A2 discloses tricyclic derivatives as androgen receptor modulators.

Published International PCT Application WO 03/011824 A1 discloses bicyclic modulators of the androgen receptor.

Published International PCT Application WO 04/041782 discloses indole derivative molecules as modulators of the androgen receptor.

Published International PCT Application WO 03/0114420 discloses fused heterocyclic derivative molecules as modulators of the androgen receptor.

Published International PCT Application WO 03/096980 discloses N-aryl hydantoin derivative molecules as modulators of the androgen receptor.

Published International PCT Application 03/011824 discloses N-naphthyl hydantoin derivative molecules as modulators of the androgen receptor.

Published International PCT Application 04/016576 discloses N-naphthyl pyrrolidine derivative molecules as modulators of the androgen receptor.

Published International PCT Application 05/000795 discloses aniline derivative molecules as modulators of the androgen receptor.

SUMMARY OF THE INVENTION

The present invention is directed to the discovery that certain substituted N-aryl pyrrolidine derivative compounds, as defined below, are modulators of the androgen receptor. Accordingly, the present invention provides a compound of the formula:

Formula I

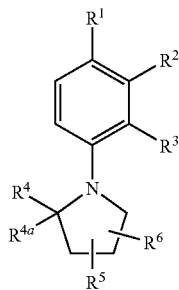

wherein,
$R^1$ represents CN, $NO_2$, $SO_2Me$, C(O)Me, CH=NOMe, or a heterocycle;
$R^2$ represents halo, halo($C_1$-$C_4$)alkyl, or ($C_1$-$C_4$)alkyl;
$R^3$ represents H or ($C_1$-$C_4$)alkyl;

$R^4$ represents an aryl, heterocycle, or benzofused heterocycle, each optionally substituted with 1-2 substituents independently selected from the group consisting of:
(a.) halo;
(b.) ($C_1$-$C_4$)alkyl;
(c.) ($C_1$-$C_4$)alkoxy;
(d.) halo($C_1$-$C_4$)alkyl;
(e.) halo($C_1$-$C_4$)alkoxy;
(f.) SR;
(g.) $SO_2R^8$;
(h.) amino;
(i.) NH—($C_1$-$C_4$)alkylamine;
(j.) N,N—($C_1$-$C_4$)dialkylamine;
(k.) $NHCOR^9$; and
(l.) $NHSO_2R^{10}$;
$R^{4a}$ represents hydrogen or methyl;
$R^5$ represents H, OH, $CH_2OH$, halo, or ($C_1$-$C_4$)alkyl;
$R^6$ represents H, OH, or ($C_1$-$C_4$)alkyl, provided that when $R^5$ and $R^6$ each represent OH, they are not bound to the same carbon atom; and
$R^7$ through $R^{10}$ each independently represent at each occurrence ($C_1$-$C_4$)alkyl, or a pharmaceutically acceptable salt thereof.

In another embodiment, the present invention provides a method of treating a disorder or condition susceptible to androgen receptor modulation, comprising administering to a patient in need thereof an effective amount of a compound of Formula I, or a pharmaceutically acceptable salt thereof. More particularly, the present invention provides a method of treating reduced muscle mass or strength, frailty, hypogonadism, osteoporosis, osteopenia, reduced bone mass or density (as occurs independently or as a result of androgen deprivation therapy), bone fractures, sarcopenia, Age Related Functional Decline (ARFD), reduced libido, male or female sexual dysfunction, erectile dysfunction, depression, prostate cancer, decreased cognitive ability, or lethargy, comprising administering to a patient in need thereof an effective amount of a compound of Formula I, or a pharmaceutically acceptable salt thereof. As a more particular aspect, the present invention provides a method for treating frailty, osteoporosis, osteopenia, prostate cancer, and male or female sexual dysfunction comprising administering to a patient in need thereof an effective amount of a compound of Formula I, or a pharmaceutically acceptable salt thereof.

Further, the present invention provides the use of a compound of Formula I, or a pharmaceutically acceptable salt thereof, as an agent for the treatment of reduced muscle mass or strength, frailty, hypogonadism, osteoporosis, osteopenia, reduced bone mass or density (as occurs independently or as a result of androgen deprivation therapy), bone fractures, sarcopenia, Age Related Functional Decline (ARFD), reduced libido, male or female sexual dysfunction, erectile dysfunction, depression, prostate cancer, decreased cognitive ability, or lethargy. More particularly, the invention provides the use of a compound of Formula I, or a pharmaceutically acceptable salt thereof, as an agent for the treatment of frailty, osteoporosis, osteopenia, or male or female sexual dysfunction.

In another embodiment, the present invention provides the use of a compound of Formula I, or a pharmaceutically acceptable salt thereof, for the manufacture of a medicament for the treatment of a disorder or condition susceptible to androgen receptor modulation. In particular, the present invention provides the use of a compound of Formula I, or a pharmaceutically acceptable salt thereof, for the manufacture of a medicament for the treatment of reduced muscle mass or strength, frailty, hypogonadism, osteoporosis, osteopenia, reduced bone mass or density (as occurs independently or as a result of androgen deprivation therapy), bone fractures, sarcopenia, Age Related Functional Decline (ARFD), reduced libido, male or female sexual dysfunction, erectile dysfunction, depression, prostate cancer, decreased cognitive ability, or lethargy. More particularly, the present invention provides the use of a compound of Formula I, or a pharmaceutically acceptable salt thereof, for the manufacture of a medicament for the treatment of frailty, osteoporosis, osteopenia, or male or female sexual dysfunction.

In addition, the present invention provides pharmaceutical compositions comprising a compound of Formula I, or a pharmaceutically acceptable salt thereof, in combination with a pharmaceutically acceptable carrier, diluent or excipient. More particularly, the present invention provides pharmaceutical compositions for the treatment of frailty, osteoporosis, osteopenia, or male or female sexual dysfunction, comprising a compound of Formula I, or a pharmaceutically acceptable salt thereof, in combination with a pharmaceutically acceptable carrier, diluent or excipient.

The present invention also encompasses novel intermediates, reagents, and processes useful for the synthesis of the compounds of Formula I, as well as a compound of Formula I for use in therapy.

DETAILED DESCRIPTION OF THE INVENTION

The present invention provides compounds with affinity for AR, which could be used to modulate (i.e., agonize, partially agonize, partially antagonize, or antagonize) receptor activity and gene expression, thereby influencing physiological functions related to Androgen hormone levels and/or AR activity. In particular, compounds of Formula (I) are potent AR ligands, which preferably agonize the androgen receptor. In addition, particularly preferred compounds of Formula (I). selectively bind to AR with greater affinity relative to the other steroid hormone receptors. More particularly, the compounds of the present invention are selective androgen receptor modulators (SARMs) which display both androgenic and antiandrogenic properties, acting as agonists of AR in some tissues while antagonizing AR in yet other tissues. Alternatively, the present invention provides as a more particular embodiment SARMs which display agonist activity in tissues such as muscle or bone, yet only partial agonist activity in tissues such as the prostate or seminal vesicles. In this regard, such ligands are believed to be useful in treating or preventing a multitude of disorders and conditions susceptible to AR modulation. Thus, methods for the treatment or prevention of disorders or conditions susceptible to AR modulation constitute an important embodiment of the present invention. As a particularly preferred aspect, the present invention provides compounds useful as SARMs.

It is also understood that many of the compounds of the present invention may exist as pharmaceutically acceptable salts and, as such, pharmaceutically acceptable salts are therefore included within the scope of the present invention. The term "pharmaceutically acceptable salt" as used herein, refers to salts of the compounds of the present invention, which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. It is further understood by the skilled reader that salt forms of pharmaceutical compounds are commonly used because they are often more readily crystallized, or more readily purified, than are the free bases. In all cases, the use of the pharmaceutical compounds of the present invention as salts is contemplated in the description herein. Hence, it is understood that where compounds of the present invention are capable of forming salts, the pharmaceutically acceptable salts and isoforms thereof are encompassed in the names or structures provided herein. Acids and bases suitable for the preparation of pharmaceutically acceptable salts, as well as procedures for preparing such salts, are well within the knowledge of those skilled in the art. See for example, Stahl et al., "Handbook of Pharmaceutical Salts: Properties, Selection and Use," VCHA/Wiley-VCH, (2002); Gould, P. L., "Salt selection for basic drugs," *International Journal of Pharmaceutics*, 33: 201-217 (1986); Berge et al., "Pharmaceutical Salts," *Journal of Pharmaceutical Sciences*, 66, No. 1, (January 1977); Bastin et al. "Salt Selection and Optimization Procedures for Pharmaceutical New Chemical Entities," *Organic Process Research and Development*, 4: 427-435 (2000).

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to one of two stereoisomers whose molecules are non-superimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The compounds of the present invention may have one or more chiral centers and may, therefore, exist in a variety of stereoisomeric configurations. As a consequence of these chiral centers the compounds of the present invention may occur as racemates, mixtures of enantiomers, and as individual enantiomers as well as diastereomers and mixtures of diastereomers. All such racemates, enantiomers, and diastereomers are within the scope of the present invention. Enantiomers of the compounds provided by the present invention can be resolved, for example, by one of ordinary skill in the art using standard techniques such as those described by J. Jacques, et al., "Enantiomers, Racemates, and Resolutions", John Wiley and Sons, Inc., 1981. The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond from the chiral carbon toward the lowest priority group. The term "S" (sinister) refers to that configuration of a chiral center with a counterclockwise relationship of group priorities (highest to second lowest) when viewed along the bond from the chiral carbon toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120.

The specific stereoisomers and enantiomers of compounds of the present invention can be prepared by one of ordinary skill in the art utilizing well known techniques and processes, such as those disclosed by Eliel and Wilen, "Stereochemistry of Organic Compounds", John Wiley & Sons, Inc., 1994, Chapter 7; Separation of Stereoisomers, Resolution, Racemization; and by Collet and Wilen, "Enantiomers, Racemates, and Resolutions", John Wiley & Sons, Inc., 1981. For example, specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of Formula I can be resolved by one of ordinary skill in the art using standard techniques well known in the art, such as those described by J. Jacques, et al., "Enantiomers, Racemates, and Resolutions", John Wiley and Sons, Inc., 1981.

Where used herein, the term "Pg" refers to a suitable oxygen or nitrogen protecting group. Suitable oxygen or nitrogen protecting groups, as used herein, refers to those groups intended to protect or block the oxygen or nitrogen group against undesirable reactions during synthetic procedures. Whether the term "Pg", as used herein, represents an oxygen protecting group or a nitrogen protecting group will be readily apparent to the ordinarily skilled artisan. The suitability of the oxygen or nitrogen protecting group used will depend upon the conditions that will be employed in subsequent reaction steps wherein protection is required, and is well within the knowledge of one of ordinary skill in the art. Commonly used nitrogen and oxygen protecting groups are disclosed in Greene, "Protective Groups In Organic Synthesis, 3$^{rd}$ Edition" (John Wiley & Sons, New York (1999)).

As used herein, the following terms have the meanings indicated: "i.v." refers to intravenously; "p.o." refers to orally; "i.p." refers to intraperitoneally; "s.c." refers to subcutaneously; "eq" or "equiv." refers to equivalents; "g" refers to grams; "Kg" refers to kilograms; "mg" refers to milligrams; "μg" refers to micrograms; "L" refers to liters; "mL" refers to milliliters; "μL" refers to microliters; "mol" refers to moles; "mmol" refers to millimoles; "M" refers to molar; "mM" refers to millimolar; "nM" refers to nanomolar; "μM" refers to micromolar; "psi" refers to pounds per square inch; "mm Hg" refers to millimeters of mercury; "min" refers to minutes; "h" or "hr" or "hrs." refers to hours; "° C." refers to degrees Celsius; "δ" refers to part per million down-field from tetramethylsilane; "MHz" refers to megahertz; "CDCl$_3$" refers to chloroform-d; "THF" refers to tetrahydrofuran; "DMF" refers to N,N-dimethylformamide; "DMSO" refers to dimethyl sulfoxide; "EtOAc" refers to ethyl acetate; "MeOH" refers to methanol; "MgSO$_4$" refers to magnesium sulfate; "LDA" refers to lithium diisopropylamide; "CH$_2$Cl$_2$" refers to dichloromethane; "NH$_4$OH" refers to ammonium hydroxide; "BEMP" refers to 2-Tert-butylimino-2-diethylamino-1,3-dimethyl-perhydro-1,3,2-diazaphosphorine; "P-BEMP" refers to Polymer supported BEMP; and TBTU refers to O-Benzotriazole-1yl)-N,N,N',N'-tetramethyluronium tetrafluoroborate.

Also as used herein, "K$_d$" refers to the equilibrium dissociation constant for a ligand-receptor complex; "K$_i$" refers to the equilibrium dissociation constant for drug-receptor complex, and is an indication of concentration of drug that will bind to half the binding sites at equilibrium; "IC$_{50}$" refers to the dose of an administered therapeutic agent which produces a 50% reduction; and "EC50" refers to the dose of an administered therapeutic agent which produce a 50% response.

As used herein the term "(C$_1$-C$_4$)alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "(C$_1$-C$_6$)alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like. It is understood that the term "(C$_1$-C$_4$)alkyl" is included within the definition of "(C$_1$-C$_6$)alkyl".

As used herein, the terms "Me", "Et", "Pr", "i-Pr", "Bu" and "t-Bu" refer to methyl, ethyl, propyl, isopropyl, butyl and tert-butyl respectively.

As used herein, the term "(C$_1$-C$_4$)alkoxy" refers to an oxygen atom bearing a straight or branched, monovalent, saturated aliphatic chain of 1 to 4 carbon atoms and includes, but is not limited to methoxy, ethoxy, n-propoxy, isopropoxy, n-butoxy, and the like. As used herein the term "(C$_1$-C$_6$)alkoxy" refers to an oxygen atom bearing a straight or branched, monovalent, saturated aliphatic chain of 1 to 6 carbon atoms and includes, but is not limited to methoxy, ethoxy, n-propoxy, isopropoxy, n-butoxy, n-pentoxy, n-hexoxy, and the like. It is understood that the term "(C$_1$-C$_4$)alkoxy" is included within the definition of "(C$_1$-C$_6$)alkoxy".

As used herein, the terms "halo", "halide" or "hal" or "Hal" refer to a chlorine, bromine, iodine or fluorine atom, unless otherwise specified herein.

As used herein, the term "halo(C$_1$-C$_4$)alkyl" refers to a straight or branched, monovalent, saturated aliphatic chain of 1 to 4 carbon atoms bearing one or more halo groups attached to one or more of the carbon atoms. As used herein, the term "halo(C$_1$-C$_6$)alkyl" refers to a straight or branched, monovalent, saturated aliphatic chain of 1 to 6 carbon atoms bearing one or more halo groups attached to one or more of the carbon atoms. It is understood that the term "halo(C$_1$-C$_4$)alkyl" is included within the definition of "halo(C$_1$-C$_6$)alkyl". Typical examples of "halo(C$_1$-C$_4$)alkyl" or "halo(C$_1$-C$_6$)alkyl" include CF$_3$, CHF$_2$, CH$_2$F, and the like. As used herein, the term "halo(C$_1$-C$_4$)alkoxy" refers to an oxygen atom bearing a straight or branched, monovalent, saturated aliphatic chain of 1 to 4 carbon atoms, further bearing one or more halo groups attached to one or more of the carbon atoms. As used herein, the term "halo(C$_1$-C$_6$)alkoxy" refers to an oxygen atom bearing a straight or branched, monovalent, saturated aliphatic chain of 1 to 6 carbon atoms, further bearing one or more halo groups attached to one or more of the carbon atoms. It is understood that the term "halo(C$_1$-C$_4$)alkoxy" is included within the definition of "halo(C$_1$-C$_6$)alkoxy". Typical examples of "halo(C$_1$-C$_4$)alkoxy" or "halo(C$_1$-C$_6$)alkoxy" include OCF$_3$, OCHF$_2$, OCH$_2$F, and the like.

As used herein, the term "aryl" refers to a monovalent aromatic carbocyclic radical and includes groups such as phenyl, naphthyl and the like.

As used herein, the term "heterocyclic" or "heterocycle" refers to a 5 to 6 membered monovalent monocyclic saturated, partially saturated, or unsaturated radical containing one to four heteroatoms each independently selected from the group consisting of oxygen, sulfur, and nitrogen. It is understood that the remaining atoms of the radical are carbon and that the radical may be attached, for example to the structure of Formula I, through any atom of the cyclic system which provides for a stable structure. Examples of typical heterocyclic groups include thiophenyl, imidazolyl, pyrrazolyl, thiazolyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, thiazolidinyl, iosoxazolidinyl, pyrazolidinyl, pyrrolidinyl, piperidinyl, piperazinyl, morpholinyl, pyranyl, thiomorpholinyl, and the like.

As used herein, the term "benzofused heterocyclic" or "benzofused heterocycle" refers to a 5 to 6 membered heterocyclic ring fused to a phenyl group. Representative "benzofused heterocyclic" groups include benzooxazolyl, benzoimidazolyl, benzimidazolonyl, benzofuranyl, benzothiophenyl, benzothiazolyl, benzoisothiazolyl, azaindolyl, indolyl, benzoimidazolonyl, or benzo[1,3]dioxolyl, and the like. It is understood that the benzofused heterocycle may be attached, for example to the structure of Formula I, through any atom of either the heterocyclic portion or the phenyl portion of the bicyclic ring system which provides for a stable structure.

As used herein the term "N,N—($C_1$-$C_4$)dialkylamine" refers to a nitrogen atom substituted with two straight or branched, monovalent, saturated aliphatic chains of 1 to 4 carbon atoms. Included within the term "N,N—($C_1$-$C_6$)dialkylamine" are —N($CH_3$)$_2$, —N($CH_3$)$_2$, —N($CH_2CH_3$)$_2$, —N($CH_2CH_3$)$_2$, —N($CH_2CH_2CH_3$)$_2$, —N($CH_2CH_2CH_3$)$_2$, and the like. "NH—($C_1$-$C_4$)alkylamine" refers to a nitrogen atom substituted with a single straight or branched, monovalent, saturated aliphatic chains of 1 to 4 carbon atoms.

As will be appreciated by one of ordinary skill in the art, some of the heterocyclic moieties of the compounds of Formula I may exist as positional isomers and as tautomeric forms. For example, tetrazole is known to exist as tautomeric structures:

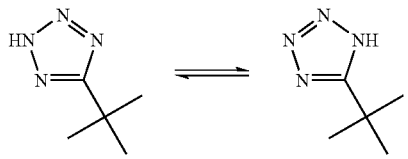

Similarly, triazoles exist in two positional isomeric forms, the 1,2,4-triazole and the 1,2,3-triazole. Each form of which may exist as tautomeric structures. The present invention contemplates all positional isomers, individual tautomeric forms, as well as any combination thereof.

The designation "—◼" refers to a bond that protrudes forward out of the plane of the page.

The designation "⋯⋯⋯" refers to a bond that protrudes backward out of the plane of the page.

As used herein the term "androgen receptor" or "AR" refers to the androgen receptor subtype, of the larger class of nuclear hormone receptors, which binds the androgen hormone testosterone, as its cognate ligand. The term "androgen receptor modulator" or "androgen modulator" or "AR modulator" as used herein, refers to those nuclear hormone receptor ligands which bind to the AR subtype and modulate (i.e. agonize, partially agonize, partially antagonize, antagonize) the receptor activity. As a particular embodiment, the present invention provides selective androgen receptor modulators (SARMs) which display androgenic properties in certain tissues (e.g. muscle and/or bone) while concomitantly displaying antiandrogenic effects in other tissues such as the prostate or liver. Alternatively, SARMs of the present invention may display agonist activity in anabolic tissues such as muscle or bone, yet display only partial agonist activity or antagonist activity in tissues such as the prostate or seminal vesicles.

As appreciated by one of skill in the art, physiological disorders may present as a "chronic" condition, or an "acute" episode. The term "chronic", as used herein, means a condition of slow progress and long continuance. As such, a chronic condition is treated when it is diagnosed and treatment continued throughout the course of the disease. Conversely, the term "acute" means an exacerbated event or attack, of short course, followed by a period of remission. Thus, the treatment of pathological disorders contemplates both acute events and chronic conditions. In an acute event, compound is administered at the onset of symptoms and discontinued when the symptoms disappear. As described above, a chronic condition is treated throughout the course of the disease.

As used herein the term "patient" refers to a mammal, such a mouse, gerbil, guinea pig, rat, dog or human. It is understood, however, that the preferred patient is a human. As used herein, the terms "treating", "treatment", or "to treat" each mean to alleviate symptoms, eliminate the causation of resultant symptoms either on a temporary or permanent basis, and to prevent, slow the appearance, or reverse the progression or severity of resultant symptoms of the named disorder or condition. As such, the methods of treatment provided by this invention encompass both therapeutic and prophylactic administration.

As used herein the term "effective amount" refers to the amount or dose of the compound, upon single or multiple dose administration to the patient, which provides the desired effect in the patient undergoing diagnosis or treatment. An effective amount can be readily determined by the attending diagnostician, as one skilled in the art, by the use of known techniques and by observing results obtained under analogous circumstances. In determining the effective amount or dose of compound administered, a number of factors are considered by the attending diagnostician, including, but not limited to: the species of mammal; its size, age, and general health; the degree of involvement or the severity of the disease involved; the response of the individual patient; the particular compound administered; the mode of administration; the bioavailability characteristics of the preparation administered; the dose regimen selected; the use of concomitant medication; and other relevant circumstances.

A typical daily dose will contain as an effective amount about 0.001 mg/kg to about 100 mg/kg of an active compound of the present invention. Preferably, the daily dose will contain as an effective amount about 0.05 mg/kg to about 50 mg/kg of the compound of the present invention.

Oral administration is a preferred route of administering the compounds employed in the present invention whether administered alone, or in combination with other therapeutic agents. Oral administration, however, is not the only route, nor even the only preferred route. Other preferred routes of administration include transdermal, percutaneous, pulmonary, intravenous, intramuscular, intranasal, intraperitoneal, buccal, sublingual, or intrarectal routes. Where the AR modulator is administered in combination with other compounds, one of the compounds may be administered by one route, such as oral, and the other may be administered by the transdermal, percutaneous, pulmonary, intravenous, intramuscular, intranasal, intraperitoneal, buccal, sublingual, or intrarectal route, as particular circumstances require. The route of administration may be varied in any way, limited by the physical properties of the compounds and the convenience of the patient and the caregiver.

The compounds employed in the present invention may be administered as pharmaceutical compositions and, therefore, pharmaceutical compositions incorporating compounds of the present invention are important embodiments of the present invention. Such compositions may take any physical form that is pharmaceutically acceptable, but orally administered pharmaceutical compositions are particularly preferred. Such pharmaceutical compositions contain, as an active ingredient, an effective amount of a compound of Formula I, including the pharmaceutically acceptable salts and hydrates thereof, which effective amount is related to the daily dose of the compound to be administered. Each dosage unit may contain the daily dose of a given compound, or may contain a fraction of the daily dose, such as one-half or one-third of the dose. The amount of each compound to be contained in each dosage unit depends on the identity of the particular compound chosen for the therapy, and other factors such as the indication for which it is given. The pharmaceutical compositions of the present invention may be formulated so as to provide quick, sustained, or delayed release of the active ingredient after administration to the patient by employing well known procedures.

The following discussion provides typical procedures for preparing pharmaceutical compositions incorporating the compounds of the present invention. However, the following is in no way intended to limit the scope of the pharmaceutical compositions provided by the present invention.

Compositions are preferably formulated in a unit dosage form, each dosage containing from about 1 to about 500 mg of each compound individually or in a single unit dosage form, more preferably about 5 to about 300 mg (for example 25 mg). The term "unit dosage form" refers to a physically discrete unit suitable as unitary dosages for a patient, each unit containing a predetermined quantity of active material calculated to produce the desired therapeutic effect, in association with a suitable pharmaceutical carrier, diluent, or excipient.

The inert ingredients and manner of formulation of the pharmaceutical compositions are conventional. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired doses and the type of composition to be used. The amount of the compound, however, is best defined as the "effective amount", that is, the amount or dose of each compound which provides the desired effect to the patient in need of such treatment. The activity of the compounds employed in the present invention does not depend on the nature of the composition, hence, the compositions are chosen and formulated solely for convenience and economy.

Capsules are prepared by mixing the compound with a suitable diluent and filling the proper amount of the mixture in capsules. The usual diluents include inert powdered substances such as starches, powdered cellulose especially crystalline and microcrystalline cellulose, sugars such as fructose, mannitol and sucrose, grain flours, and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

Tablets are often coated with sugar as a flavor and sealant. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

A lubricant is often necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acid contents of the stomach. Such formulations are created by coating a solid dosage form with a film of a polymer which is insoluble in acid environments, and soluble in basic environments. Exemplary films are cellulose acetate phthalate, polyvinyl acetate phthalate, hydroxypropyl methylcellulose phthalate and hydroxypropyl methylcellulose acetate succinate.

When it is desired to administer the compound as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

It is understood by one of ordinary skill in the art that the procedures as described above can also be readily applied to a method of treating disorders susceptible to androgen receptor modulation, and particularly frailty, osteoporosis, osteopenia, and male or female sexual dysfunction.

When used in conjunction with the methods and uses of the present invention, the compounds and compositions of the present invention may be administered either alone, or in combination with conventional therapeutic agents used to treat the particular disorder or condition. Where the compounds or compositions of the present invention are used as part of a combination, the compound or composition comprising Formula I may be administered separately or as part of a formulation comprising the therapeutic agent with which it is to be combined.

Combination Therapy for Osteoporosis:

Conventional therapeutic agents for the treatment of osteoporosis may advantageously be combined with the compounds of Formula I, or compositions comprising a compound of Formula I. Conventional agents for the treatment of osteoporosis include hormone replacement therapies such as conjugated equine estrogen (Premarin®), synthetic conjugated estrogen (Cenestin®), esterified estrogen (Estratab® or Menest®), estropiate (Ogen® or Ortho-est®); as well as transdermal estradiol preparations such as Alora®, Climara®, Estraderm®, and Vivelle®. Combination estrogen-progestin formulations are also available for the treatment of osteoporosis including Prempro® (conjugated equine estrogen and medroxyprogesterone acetate), Premphase® (conjugated equine estrogen and norgestimate), Ortho-Prefest® (estradiol and norgestimate), Femhrt® (ethinyl estradiol and norethindrone acetate), and Combipatch (transdermal estradiol and norethindrone acetate). Other conventional osteoporosis treatments which may be combined with the compounds or compositions of the present invention include bisphosphonates such as alendronate (Fosamax®), risedronate (Actonel®), and pamidronate (Aredia®); selective estrogen receptor modulators (SERMs) such as raloxifene (Evista®); calcitonin (Calcimar® or Miacalcin®); parathyroid hormone (Forteo®); calcium; Vitamin D; diuretics (to reduce $Ca^{2+}$ excretion); fluoride; and androgens (testosterone or 5α-dihydrotestosterone).

Thus, a formulation for combination therapy in treating osteoporosis comprises:

Ingredient (A1): a compound of Formula I;
Ingredient (A2): one or more co-agents that are conventional for the treatment of osteoporosis selected from the group consisting of Premarin®, Cenestin®, Estratab®, Menest®, Ogen®, Ortho-est®, Alora®, Climara®, Estraderm®, Vivelle®, Prempro®, Premphase®, Ortho-Prefest®, Femhrt®, Combipatch®, Fosamax®), Actonel®, Aredia®); Evista®; Calcimar®, Miacalcin®, Forteo®, calcium, Vitamin D, diuretics, fluoride, testosterone, and 5α-dihydrotestosterone;
and optionally
Ingredient (A3): a pharmaceutically acceptable carrier, diluent or excipient.

PARTICULAR ASPECTS OF THE INVENTION

The following list sets out several groupings of particular substituents and particular variables for compounds of Formula I. It will be understood that compounds of Formula I having such particular substituents or variables, as well as methods and uses employing such compounds, represent particular aspects of the present invention. It will be further understood that each of these groupings of particular substituents and particular variables may be combined with other provided groupings, to create still additional particular aspects of the compounds, methods and uses of the present invention.

Thus, a particular aspect of the present invention is one wherein the compound of Formula I, is one wherein:
(a) $R^1$ represents CN, $NO_2$, $SO_2Me$, C(O)Me, or CH=NOMe;
(b) $R^1$ represents CN, $NO_2$, $SO_2Me$, or C(O)Me;
(c) $R^1$ represents CN, $NO_2$, or $SO_2Me$;
(d) $R^1$ represents CN or CH=NOMe; or
(e) $R^1$ represents CN.

Additional particular aspects of the present invention are those wherein the compound of Formula I, is one wherein
(a) $R^2$ represents fluoro, chloro, bromo, halo($C_1$-$C_4$)alkyl, or methyl;
(b) $R^2$ represents fluoro, chloro, bromo, or halo($C_1$-$C_4$)alkyl;
(c) $R^2$ represents fluoro, chloro, bromo, difluoromethyl, trifluoromethyl, or methyl;
(d) $R^2$ represents fluoro, chloro, bromo, difluoromethyl, or trifluoromethyl;
(e) $R^2$ represents chloro, difluoromethyl, or trifluoromethyl;
(f) $R^2$ represents chloro, or trifluoromethyl,
(g) $R^2$ represents chloro; or
(h) $R^2$ represents trifluoromethyl.

Additional particular aspects of the present invention are those wherein the compound of Formula I, is one wherein
(a) $R^3$ represents hydrogen, methyl, ethyl, propyl, isopropyl, isobutyl, or tert-butyl;
(b) $R^3$ represents hydrogen, methyl, ethyl, propyl, isopropyl, or tert-butyl;
(c) $R^3$ represents hydrogen, methyl, or ethyl,
(d) $R^3$ represents hydrogen, or methyl,
(e) $R^3$ represents hydrogen; or
(f) $R^3$ represents methyl Additional particular aspects of the present invention are those wherein the compound of Formula I, is one wherein
(a) $R^4$ represents an aryl, heterocycle, or benzofused heterocycle selected from the group consisting of phenyl, thiophenyl, imidazolyl, pyrrazolyl, thiazolyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, thiazolidinyl, iosoxazolidinyl, pyrazolidinyl, pyrrolidinyl, piperidinyl, piperazinyl, morpholinyl, pyranyl, thiomorpholinyl, benzooxazolyl, benzoimidazolyl, benzofuranyl, benzothiophenyl, benzothiazolyl, benzoisothiazolyl, azaindolyl, and indolyl, benzoimidazolonyl, or benzo[1,3]dioxolyl, each optionally substituted with 1-2 substituents independently selected from the group consisting of halo, ($C_1$-$C_4$)alkyl, ($C_1$-$C_4$)alkoxy, halo($C_1$-$C_4$)alkyl, halo($C_1$-$C_4$)alkoxy, —$SR^7$, —$SO_2R^8$, amino, NH—($C_1$-$C_4$)alkylamine, N,N—($C_1$-$C_4$)dialkylamine, $NHCOR^9$, and $NHSO_2R^{10}$;
(b) $R^4$ represents an aryl, heterocycle, or benzofused heterocycle selected from the group consisting of phenyl, thiophenyl, imidazolyl, pyrrazolyl, thiazolyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, thiazolidinyl, iosoxazolidinyl, pyrazolidinyl, pyrrolidinyl, piperidinyl, piperazinyl, morpholinyl, pyranyl, thiomorpholinyl, benzooxazolyl, benzoimidazolyl, benzofuranyl, benzothiophenyl, benzothiazolyl, benzoisothiazolyl, azaindolyl, and indolyl, benzoimidazolonyl, or benzo[1,3]dioxolyl, each optionally substituted with a substituent selected from the group consisting of halo, ($C_1$-$C_4$) alkyl, ($C_1$-$C_4$)alkoxy, halo($C_1$-$C_4$)alkyl, halo($C_1$-$C_4$) alkoxy, —$SR^7$, —$SO_2R^8$, amino, NH—($C_1$-$C_4$) alkylamine, N,N—($C_1$-$C_4$)dialkylamine, $NHCOR^9$, and $NHSO_2R^{10}$;
(c) $R^4$ represents an aryl, heterocycle, or benzofused heterocycle selected from the group consisting of phenyl, thiophenyl, imidazolyl, pyrrazolyl, thiazolyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, thiazolidinyl, iosoxazolidinyl, pyrazolidinyl, pyrrolidinyl, piperidinyl, piperazinyl, morpholinyl, pyranyl, thiomorpholinyl, benzooxazolyl, benzoimidazolyl, benzofuranyl, benzothiophenyl, benzothiazolyl, benzoisothiazolyl, azaindolyl, and indolyl, benzoimidazolonyl, or benzo[1,3]dioxolyl, optionally substituted with a substituent selected from the group consisting of halo, methyl, ethyl, methoxy, ethoxy, $CF_3$, $CHF_2$, $OCF_3$, —$SR^7$, and —$SO_2R^8$;
(d) $R^4$ represents an aryl, heterocycle, or benzofused heterocycle selected from the group consisting of phenyl, thiophenyl, imidazolyl, pyrrazolyl, thiazolyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, thiazolidinyl, iosoxazolidinyl, pyrazolidinyl, pyrrolidinyl, piperidinyl, piperazinyl, morpholinyl, pyranyl, thiomorpholinyl, benzooxazolyl, benzoimidazolyl, benzofuranyl, benzothiophenyl, benzothiazolyl, benzoisothiazolyl, azaindolyl, and indolyl, benzoimidazolonyl, or benzo[1,3]dioxolyl, each optionally substituted with a substituent selected from the group consisting of fluoro, methyl, methoxy, CHF2, CF3, OCF3, SMe, SO2Me, amino, NHCOMe, and NHSO2Me;

(e) $R^4$ represents an aryl, heterocycle, or benzofused heterocycle selected from the group consisting of phenyl, pyridinyl, pyrimidinyl, or benzo[1,3]dioxolyl, optionally substituted with a substituent selected from the group consisting halo, methyl, ethyl, methoxy, ethoxy, $CF_3$, $CHF_2$, $OCF_3$, $-SR^7$, and $-SO_2R^8$;

(f) $R^4$ represents an aryl, heterocycle, or benzofused heterocycle selected from the group consisting of phenyl, pyridinyl, pyrimidinyl, or benzo[1,3]dioxolyl, optionally substituted with a substituent selected from the group consisting of fluoro, chloro, methoxy, $CF_3$, SMe, $SO_2Me$, amino, $N(Me)_2$, NHCOMe, and $NHSO_2Me$;

(g) $R^4$ represents an aryl, heterocycle, or benzofused heterocycle selected from the group consisting of phenyl, pyridinyl, pyrimidinyl, or benzo[1,3]dioxolyl, optionally substituted a substituent selected from the group consisting of fluoro, chloro, methoxy, $CF_3$, SMe, and $SO_2Me$;

(h) $R^4$ represents a group of the formula:

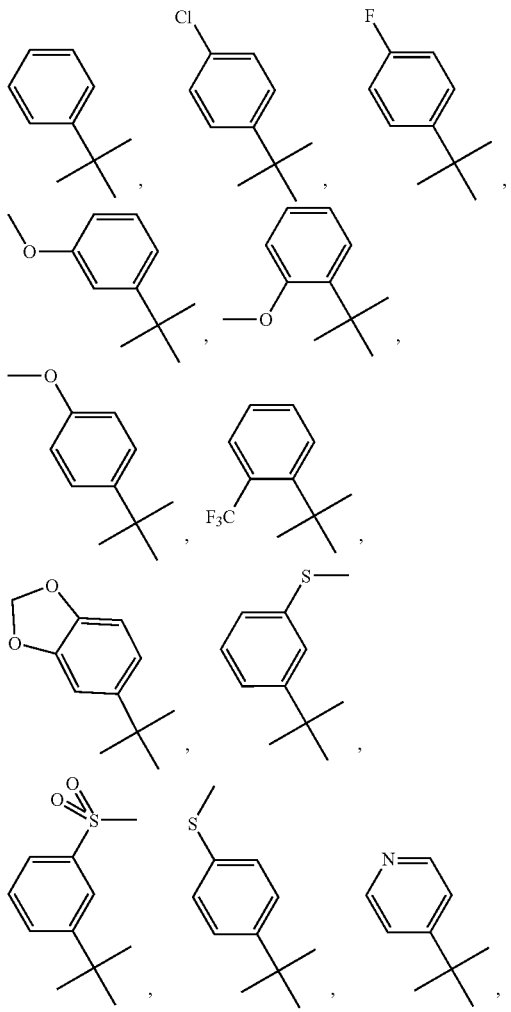

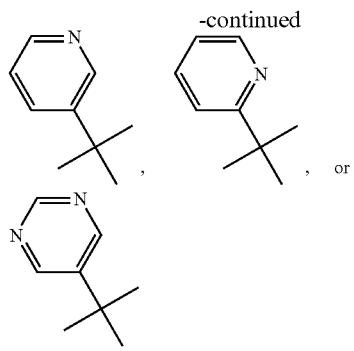

Yet additional particular aspects of the present invention are those wherein the compound of Formula I, is one wherein
(a) $R^5$ represents hydrogen, halo, hydroxy, CH2OH, or methyl;
(b) $R^5$ represents hydrogen, halo, hydroxy, or $(C_1-C_4)$alkyl;
(c) $R^5$ represents hydrogen, hydroxy, or methyl;
(d) $R^5$ represents hydrogen, fluoro, or chloro;
(e) $R^5$ represents hydrogen or hydroxy;
(f) $R^5$ represents hydrogen, methyl, or ethyl;
(g) $R^5$ represents hydrogen or methyl;
(h) $R^5$ represents hydrogen; or
(i) $R^5$ represents methyl.

Still additional particular aspects of the present invention are those wherein the compound of Formula I, is one wherein
(a) $R^6$ represents hydrogen, OH, methyl, or ethyl;
(b) $R^6$ represents hydrogen, OH, or methyl;
(c) $R^6$ represents hydrogen, methyl, or ethyl
(d) $R^6$ represents hydrogen or methyl;
(e) $R^6$ represents hydrogen; or
(f) $R^6$ represents methyl.

As an even more particular aspect, the present invention provides a compound of Formula I, wherein,
R1 represents CN or CH=NOMe;
R2 represents halo, $CF_3$, or methyl;
R3 represents H, methyl or ethyl;
R4 represents an aryl, heterocycle, or benzofused heterocycle selected from the group consisting of phenyl, thiophenyl, imidazolyl, pyrrazolyl, thiazolyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, thiazolidinyl, iosoxazolidinyl, pyrazolidinyl, pyrrolidinyl, piperidinyl, piperazinyl, morpholinyl, pyranyl, thiomorpholinyl, benzooxazolyl, benzoimidazolyl, benzofuranyl, benzothiophenyl, benzothiazolyl, benzoisothiazolyl, azaindolyl, and indolyl, benzoimidazolonyl, or benzo[1,3]dioxolyl, each optionally substituted with 1-2 substituents independently selected from the group consisting of halo, methyl, ethyl, methoxy, $CHF_2$, $CF_3$, $OCF_3$, SMe, $SO_2Me$, amino, NHMe, $N(Me)_2$, NHCOMe, or $NHSO_2Me$;
R4a represents hydrogen or methyl;
R5 represents H, OH, $CH_2OH$, or methyl; and
R6 represents H, OH, or methyl, provided that when R5 and R6 each represent OH, they are not bound to the same carbon atom,
or a pharmaceutically acceptable salt thereof.

As an even further particular aspect, the present invention provides a compound of Formula I wherein,
R1 represents CN or CH=NOMe;
R2 represents halo or $CF_3$;
R3 represents H, methyl or ethyl;
R4 represents an aryl, heterocycle, or benzofused heterocycle selected from the group consisting of phenyl, thiophenyl, imidazolyl, pyrrazolyl, thiazolyl, isothiazolyl, oxazolyl, isoxazolyl, triazolyl, thiadiazolyl, oxadiazolyl, tetrazolyl, pyridyl, pyridinyl, pyrimidyl, pyrazinyl, pyridiazinyl, triazinyl, thiazolidinyl, iosoxazolidinyl, pyrazolidinyl, pyrrolidinyl, piperidinyl, piperazinyl, morpholinyl, pyranyl, thiomorpholinyl, benzooxazolyl, benzoimidazolyl, benzofuranyl, benzothiophenyl, benzothiazolyl, benzoisothiazolyl, azaindolyl, and indolyl, benzoimidazolonyl, or benzo[1,3]dioxolyl, each optionally substituted with a substituent selected from the group consisting of halo, methyl, ethyl, methoxy, $CHF_2$, $CF_3$, $OCF_3$, SMe, $SO_2Me$, amino, NHMe, $N(Me)_2$, NHCOMe, and $NHSO_2Me$;

R4a represents hydrogen or methyl;

R5 represents H, OH, $CH_2OH$, or methyl; and

R6 represents H, OH, or methyl, provided that when R5 and R6 each represent OH, they are not bound to the same carbon atom, or a pharmaceutically acceptable salt thereof.

Further still, the present invention provides a compound of Formula I wherein R1 represents CN; R2 represents Cl or CF3; R3 represents H or methyl; R4 represents phenyl, pyridinyl, pyrimidinyl, or benzo[1,3]dioxolyl, each optionally substituted a substituent selected from the group consisting of fluoro, chloro, methyl, methoxy, $CHF_2$, $CF_3$, $OCF_3$, SMe, $SO_2Me$, amino, NHCOMe, and $NHSO_2Me$; R4a represents H or methyl; R5 represents H, OH, or methyl; and R6 represents H or methyl, or a pharmaceutically acceptable salt thereof.

As a most particular aspect, the present invention provides a compound of Formula I wherein R1 represents CN; R2 represents Cl; R3 represents H or methyl; R4 represents a group of the formula

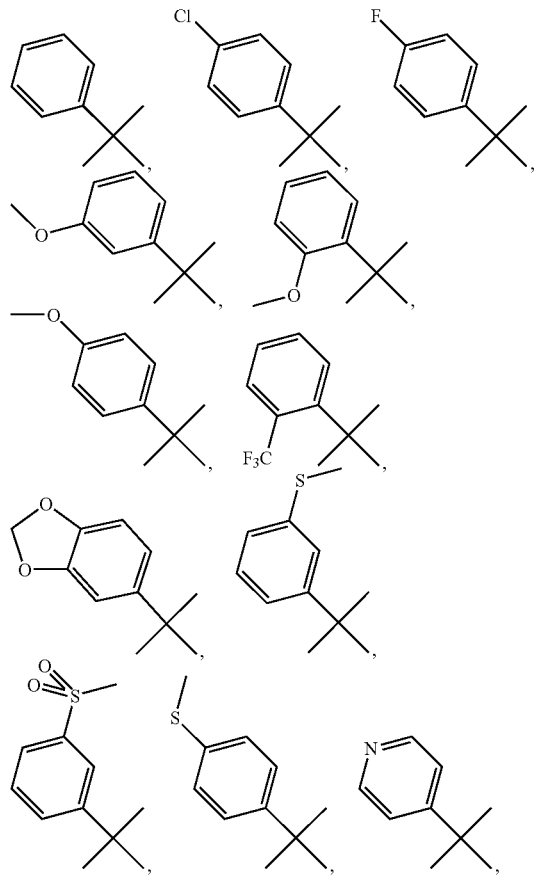

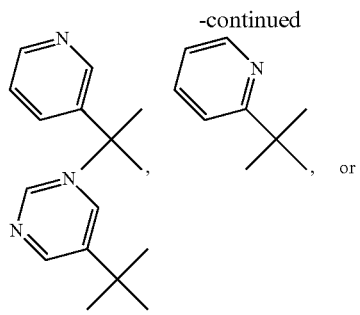

R4a represents H or methyl; R5 represents H or methyl; and R6 represents H or methyl, or a pharmaceutically acceptable salt thereof.

In addition, it will be understood a most particular aspect of the present invention is provided by those compounds of Formula I exemplified herein.

All of the compounds of the present invention can be chemically prepared, for example, by following the synthetic routes set forth in the Schemes and/or the Preparations and Examples below. However, the following discussion is not intended to be limiting to the scope of the present invention in any way. For example, the specific synthetic steps for each of the routes described may be combined in different ways, or in conjunction with steps from different schemes, to prepare additional compounds of Formula I All substituents, unless otherwise indicated, are as previously defined. The reagents and starting materials are readily available to one of ordinary skill in the art. For example, certain 2-aryl or 2-heterocyclic pyrrolidines such as 4,4-dimethyl-2-phenyl-pyrrolidine, 2-(4-chlorophenyl)-pyrrolidine, and 3-(2-pyrrolidinyl)pyridine are available commercially or have been described in the literature. In addition, procedures for making intermediates or examples are provided in Giovannini, A., Savoia, D., Umani-Ronchi, A. *J. Org. Chem.* (1989), 54, 228-234; Rho, T., Abuh, Y. F. *Synth. Commun.* (1994), 24, 253-256; Elslager, E. F., Johnson, J. L., Werbel, L. M. *J. Med. Chem.* (1981), 24, 140-145; Anderson, A. G., Willis, M. T. *J. Org. Chem.* (1967), 32, 3241-3243.

Other necessary reagents and starting materials may be made by procedures which are selected from standard techniques of organic and heterocyclic chemistry, techniques which are analogous to the syntheses of known structurally similar compounds, and the procedures described in the Examples below, including any novel procedures. It will be recognized that in addition to the methods described herein, that the literature contains variations of these methods or alternate methods. For example, 5-aryl-3,4-dihydro-2H-pyrroles can be obtained using procedures such as those described by: Dekimpe, N., Tehrani, K. A., Stevens, C., Decooman, P. *Tetrahedron* (1997), 53, 3693; Coindet, C., Comel, A., Kirsch, G. *Tetrahedron Lett.* (2001), 42, 6101; Keppens, M., De Kimpe, N., Fonck, G. *Synth. Comm.* (1996), 26, 3097; Fry, D. F., Fowler, C. B., Dieter, R. K. *Synlett* (October 1994), 836.

Scheme I

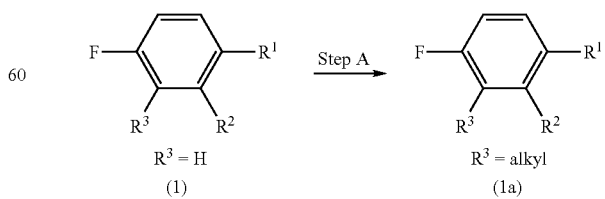

In Scheme I, Step A, a substituted benzene-derivative of formula (1) wherein $R^3$=H (for example a substituted benzonitrile when $R^1$=CN), is converted to a 3-alkylbenzene derivative of formula (1a) wherein $R^3$=alkyl (for example a 3-alkylbenzonitrile). The compound of formula (1) is treated with lithium diisopropylamide at a temperature of −100 to −60° C., for about 1 to 6 hours, in an inert solvent such as tetrahydrofuran. It is recognized by one skilled in the art that lithium diisopropylamide can be obtained commercially, or preferably, can be generated in situ using n-butyl lithium and diisopropylamide at about −5 to 0° C. for 1 to 3 hours in an inert solvent such as tetrahydrofuran. The prepared lithium-diisopropylamide is then cannulated into a solution of the compound of formula (1) at a temperature of about −100 to −70° C. and maintained for about 2 to 6 hours before adding an alkyl halide, such as iodomethane. Over a period of about 10 to 15 hours the reaction is allowed to warm slowly to about −5 to 5° C. and then quenched with ammonium chloride and isolated using common extractive techniques. The product may then be purified using standard techniques such as silica gel chromatography

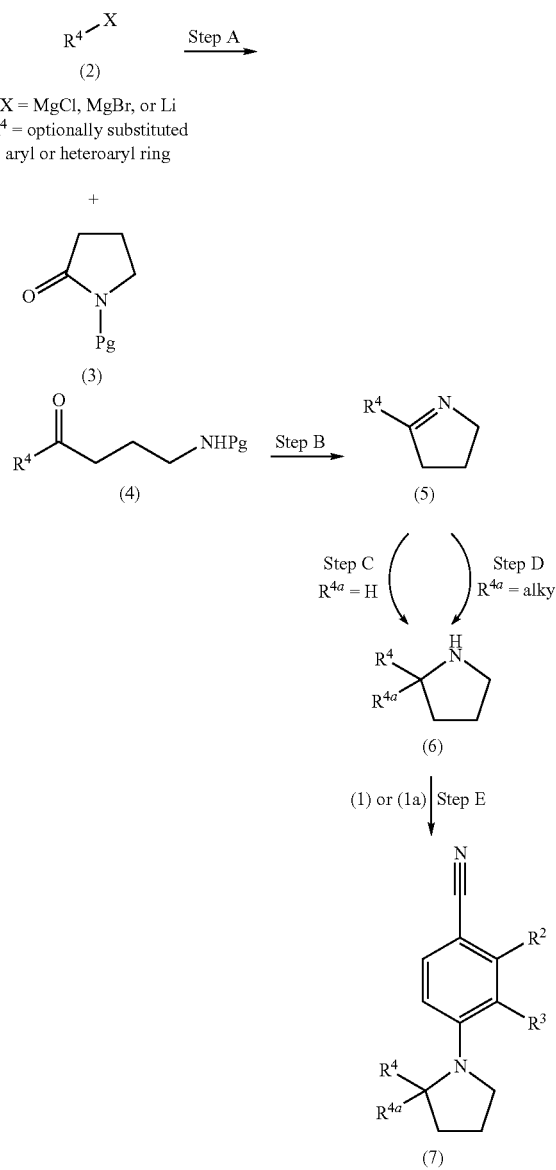

In Scheme II, Step A, an organic Grignard or lithium complex of formula (2), wherein $R^4$ is an optionally substituted aryl or heterocyclic ring, is reacted with an optionally substituted pyrrolidinone of formula (3) to obtain a 4-oxo-butyl protected amine of formula (4). It is recognized by one skilled in the art that the protecting group of formula (3) could be a variety of protecting groups such as benzyl carbamate (cbz), allyl carbamate, or tert-butyl carbamate (boc) with tert-butyl carbamate being the preferred protecting group. Aryl or heterocyclic Grignard reagents of formula (2) are commercially available, but it is recognized by one skilled in the art that Grignard reagents can be formed from the aryl or heterocyclic halide using standard techniques. In addition, an appropriate aryl or heterocyclic metal complex can be formed from the corresponding aryl or heterocyclic halide and an alkyl lithium reagent such as n-butyl lithium at a temperature of about −100° C. in an inert solvent such as tetrahydrofuran as described by Rho, T., Abuh, Y. F., Syn. Comm., (1994), 24, 253-256. It is then treated in situ with a pyrrolidinone of formula (3), which is pre-cooled to a temperature of about −100 to −70° C. for about 30 minutes to 1 hour, and then quenched with a solution of hydrogen chloride in an inert solvent, such as diethyl ether. In a similar fashion the Grignard reagent of formula (2) is added to a pyrrolidinone of formula (3) in an inert solvent such as diethyl ether or preferably, tetrahydrofuran, at a temperature of about −70° C. to −30° C. The reaction is allowed to warm to about 0° C. for about 30 minutes to 6 hours and then quenched with hydrochloric acid. The product is isolated using common extractive techniques and may be purified using standard techniques such as silica gel chromatography.

In Scheme II, Step B, a 4-oxo-butyl protected amine of formula (4) is deprotected and cyclized to give a dihydropyrtole of formula (5). The amine protecting group of formula (4) can be removed using a variety of methods, depending on the nature of the particular protecting group, using means which are common to those skilled in the art. Methods for removal of amine protecting groups can be found in Green, T. W., Wuts, P. G. M., "Protective Groups in Organic Synthesis", John Wiley & Sons, Inc (1991), 315-348. As noted above, the preferred protecting group is tert-butyl carbamate (boo). With such a boc protecting group the compound of formula (4) can be deprotected under acidic conditions such as with trifluoroacetic acid, 4N hydrogen chloride/dioxane, or 10% $H_2SO_4$ in dioxane. The preferred method uses 10-30 equivalents of trifluoroacetic acid, either neat or with a small amount of dichloromethane, at a temperature of about 0° C. for about 1 to 16 hours. After deprotection the resulting amine cyclizes in situ to give a dihydropyrrole of formula (5). The product is isolated by adjusting the reaction mixture to a basic pH and extracting with an inert organic solvent, and then may be purified using standard techniques such as silica gel chromatography.

In Scheme II, Step C, a dihydropyrrole of formula (5) is reduced to a pyrrolidine of formula (6) (wherein $R^{4a}$ is hydrogen). It will be recognized by one of ordinary skill in the art that an enamine such as that found in formula (5) can be reduced using a variety of methods. For example the reduction can be accomplished by hydrogenation over Pd on carbon, sodium borohydride, sodium cyanoborohydride, or other metal hydrides such as lithium aluminum hydride or diisobutylaluminum hydride. The preferred method uses 1 to 5 equivalents of sodium cyanoborohydride with 1 to 5 equivalents of acetic acid in a protic solvent such as ethanol. The reaction is maintained at about 0 to 60° C. for about 1 to 48 hours. The product is isolated by addition of an aqueous inorganic base, and extraction with an inert solvent. The product may then be purified using standard techniques such as silica gel chromatography and acid/base extractive techniques common to one skilled in the art.

In Scheme II, Step D, a dihydropyrrole of formula (5) is treated with an alkyl lithium reagent to provide a pyrrolidine of formula (6) (wherein $R^{4a}$ represents an alkyl, such as methyl or ethyl). For example, a dihydropyrrole of formula (5) is treated at about −80 to −60° C. in an inert solvent such as tetrahydrofuran with a Lewis acid, such as boron trifluoride diethyl etherate for a period of about 15 to 60 minutes. An alkyl Grignard reagent or alkyl lithium is added, with methyl lithium being preferred. The temperature is maintained at about −80 to −60° C. for 1 to 3 hours and then allowed to warm to ambient temperature over 1 to 24 hours. The product can be isolated by common extractive techniques known to one skilled in the art, such as quenching with ammonium chloride solution, treatment with an aqueous inorganic base, such as sodium hydroxide, followed by extraction with an inert solvent. The product may then be purified by standard techniques such as silica gel chromatography.

In Scheme II, Step E, an optionally substituted 4-fluorobenzonitrile of formula (1) or (1a), is displaced with a pyrrolidine of formula (6) to give a N-aryl pyrrolidine of formula (7). Methods for accomplishing an aromatic nucleophilic substitution are well known to those skilled in the art or the reader may consult the text of R. C. Larock in "Comprehensive Organic Transformations", VCH Publishers, 1989, p. 397-398. The preferred method is to mix the benzonitrile of formula (1) or (1a), and the pyrrolidine of formula (6), neat with an organic base, such as N-methylmorpholine or diisopropylethylamine at a temperature of about 100 to 180° C. The preferred temperature is about 150° C. for about 4 to 48 hours. The product is isolated directly by silica gel chromatography.

-continued

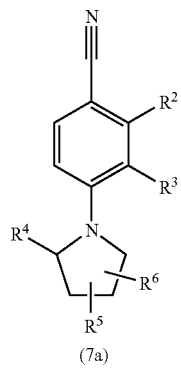

(7a)

Scheme IIa depicts synthetic methodology wherein additional substitution on the pyrrolidine ring, groups $R^5$ and $R^6$, may be introduced earlier in the sequence. It will be recognized by one skilled in the art that various substituted pyrrolidinones of formula (3a) can be obtained by various methods as described in the literature. The pyrrolidine of formula (6a) is prepared using Steps A, B, and C essentially as described previously for Scheme II. The compound of structure (6a) is then treated with a compound of formula 1 or 1a in Step E (also as described in Scheme II) to produce the compound of structure (7a). It will be recognized by one skilled in the art that various protecting group combinations and strategies can be utilized to accommodate $R^5$ and $R^6$ in order to obtain products of formula (7a).

Scheme IIa

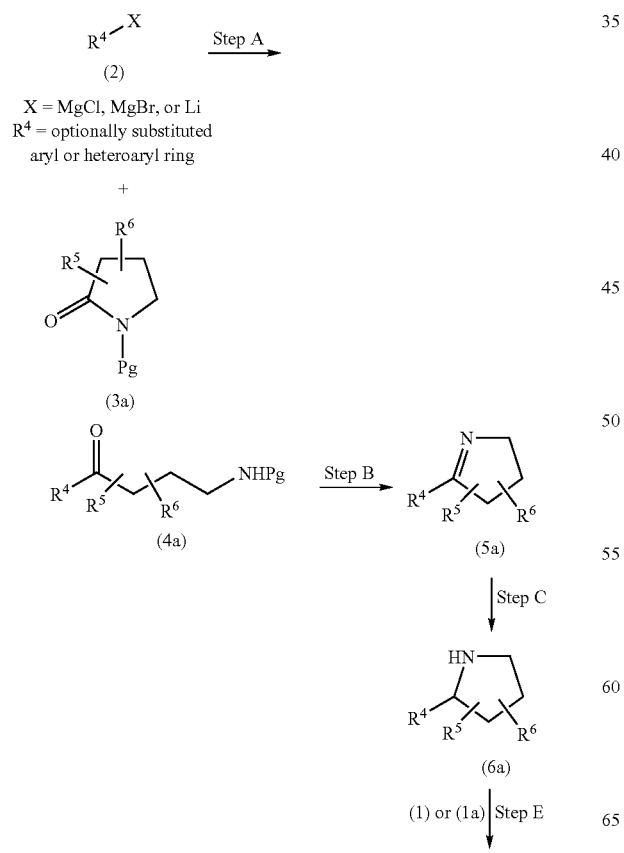

Scheme III

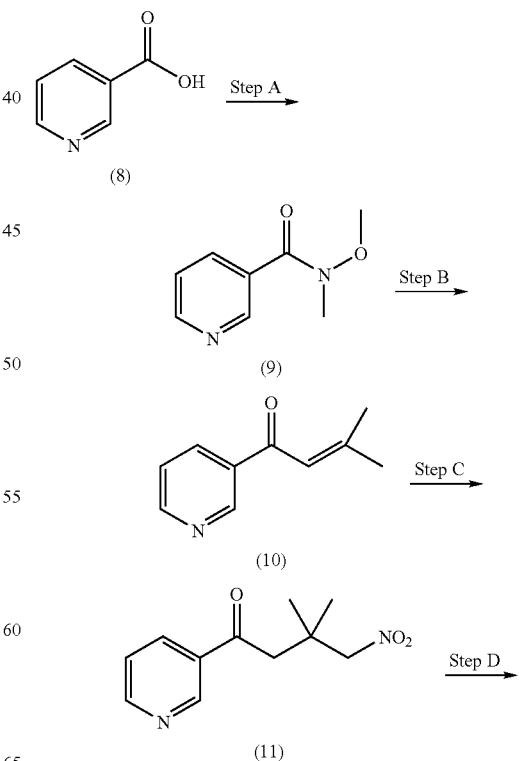

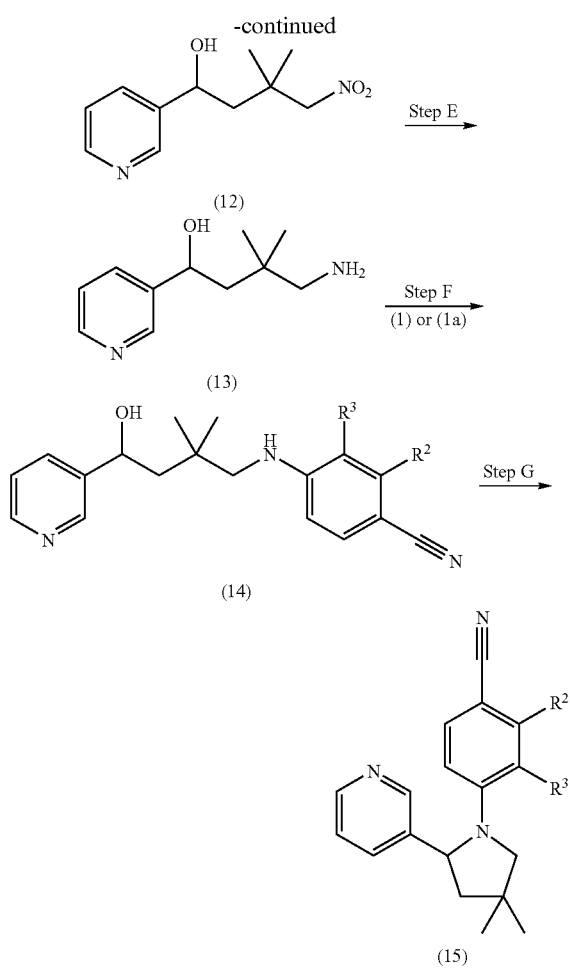

In Scheme III, Step A, nicotinic acid is converted to a Weinreb amide, the pyridine amide of formula (8). The nicotinic acid is activated using HOBT and EDCI and treated with N,O-dimethylhydroxylamine hydrochloride in the presence of triethylamine. The reaction is performed in an inert solvent, such as acetonitrile, for 1 to 12 hours at ambient temperature. The product is isolated using extractive techniques known in the art.

In Scheme III, Step B, the pyridine amide of formula (9) is converted to the butenone of formula. (10) using 2-methyl propenyl magnesium bromide. The reaction is performed in an inert solvent, such as THF, at a temperature of −90 to −50° C. and allowed to warm to room temperature after one hour. After 2 to 12 h the reaction is quenched with ammonium chloride solution and extracted with an organic solvent, such as ethyl acetate.

In Scheme III, Step C, the butanone of formula (10) is converted to the nitro butanone of formula (11) by Michael addition of nitro methane in the presence of DBU. After a period of 30 min to 8 h the product is isolated using an organic solvent, such as diethyl ether with acid/base extraction techniques known to those skilled in the art.

In Scheme III, Step D, the ketone of formula (11) is reduced to the alcohol of formula (12) using sodium borohydride in methanol at room temperature for 1 to 8 h. This is followed, in Step E, by reduction of the nitro group to the amino pentanol of formula (13). The reaction is performed in a suitable solvent, such as ethanol, in the presence of a metal catalyst, such as sulfided platinum on carbon (Pt—C(S)) at room temperature under an atmosphere of hydrogen (5-8 atm) for 12 to 48 h.

In Scheme III, Step F, the amine of formula (13) reacts with an aryl fluoride in a nucleophilic aromatic substitution reaction to provide a butylamino benzonitrile of formula (14). The amine and the aryl fluoride are combined in an inert solvent such as DMF or 1-methyl-2-pyrrolidinone (NMP), with NMP being preferred, and heated in a microwave reactor for 1 to 12 h at a temperature of 100 to 140° C. The product is isolated and purified using an ion exchange resin.

In Scheme III, Step E, the butylamino benzonitrile of formula (14) is cyclized to the pyrrolidine of formula (15). The tosylate of the alcohol is formed in situ and used to alkylate the amine. The reaction is performed using tosyl chloride in pyridine and heated at a temperature of 90 to 110° C. for a period of 12 to 72 h. The pyridine is removed in vacuo and the product isolated by extractive techniques using an appropriate organic solvent. The product is purified using chromatographic techniques known in the art, such as silica gel chromatography and HPLC.

Determination of Biological Activity

To demonstrate that compounds of the present invention have affinity for the androgen receptor, and thus have the capacity to modulate androgen receptor activity, nuclear hormone receptor binding assays are first performed. All ligands, radioligands, solvents, and reagents employed in the binding assays are readily available from commercial sources, or can be readily synthesized by the ordinarily skilled artisan.

Steroid Hormone Nuclear Receptor Binding Assay:

Cell lysates from 293 cells overexpressing human GR (glucocorticoid receptor), AR (androgen receptor), MR (mineralocorticoid receptor) or PR (progesterone receptor) are used for competition binding assays to determine Ki values for test compounds. Briefly, competition binding assays are run in a buffer containing 20 mM Hepes, pH 7.6, 0.2 mM EDTA, 75 mM NaCl, 1.5 mM MgCl2, 20% glycerol, 20 mM sodium molybdate, 0.2 mM DTT, 20 ug/ml aprotinin and 20 ug/ml leupeptin, using either 0.3 nM $^3$H-dexamethasone for GR binding, 0.36 nM $^3$H-methyltrienolone for AR binding, 0.25 nM $^3$H-aldosterone for MR binding, or 0.29 nM $^3$H-methyltrienolone for PR binding, and either 20 ug 293-GR lysate, 22 ug 293-AR lysate, 20 ug 293-MR lysate or 40 ug 293-PR lysate per well. Competing compounds are added at various concentrations ranging from about 0.01 nM to 10 µM. Non-specific binding is determined in the presence of 500 nM dexamethasone for GR binding, 500 nM aldosterone for MR binding, or 500 nM methyltrienolone for AR and PR binding. The binding reaction (140 µl) is incubated for overnight at 4° C., then 70 µl of cold charcoal-dextran buffer (containing per 50 ml of assay buffer, 0.75 g of charcoal and 0.25 g of dextran) is added to each reaction. Plates are mixed 8 minutes on an orbital shaker at 4° C. Plates are then centrifuged at 3,000 rpm at 4° C. for 10 minutes. An aliquot of 120 µl of the mix is transferred to another 96-well plate and 175 µl of Wallac Optiphase "Hisafe 3" scintillation fluid is added to each well. Plates are sealed and shaken vigorously on an orbital shaker. After an incubation of 2 hrs, plates are read in a Wallac Microbeta counter. The data is used to calculate an $IC_{50}$ and % Inhibition at 10 µM. The $K_d$ for $^3$H-dexamethasone for GR binding, $^3$H-methyltrienolone for AR binding, $^3$H-aldosterone for MR binding, or $^3$H-methyltrienolone for PR binding, is determined by saturation binding. The $IC_{50}$ values for test compounds are converted to $K_i$ using Cheng-Prusoff equation and the $K_d$ determined by saturation binding assay.

Binding assay protocols for steroid hormone nuclear receptors similar to those described above can be readily designed by the ordinarily skilled artisan. Representative compounds of the present invention have a Ki in the AR binding assay of ≦5 µM. More particularly, the exemplified compounds of the present invention have a Ki in the AR binding assay of ≦1 µM. Even more particularly, exemplified compounds of the present invention have a Ki in the AR binding assay of ≦500 nM. More particular still, exemplified compounds of the present invention have a Ki in the AR binding assay of ≦100 nM. Table I (see below) provides AR binding data for a representative sample of the exemplified compounds of the present invention. In addition, particularly preferred compounds of the present invention selectively bind to the androgen receptor with greater affinity relative to the other steroid hormone receptors (MR, GR, and PR)

To demonstrate the ability of compounds of the present invention to modulate the activity of the androgen receptor (i.e. either agonize, partially agonize, partially antagonize, or antagonize), bioassays are performed which detect modulation of target gene expression in cells transiently transfected with a nuclear receptor protein and a hormone response element-reporter gene construct. The solvents, reagents, and ligands employed in the functional assay are readily available from commercial sources, or can be synthesized by one of ordinary skill in the art.

Functional Assay of Steroid Hormone Nuclear Receptor Modulation:

Human embryonic kidney hEK293 cells are co-transfected using FUGENE™. Briefly, the reporter plasmid containing two copies of probasin ARE (androgen response element 5'GGTTCTTGGAGTACT$^3$') (SEQ ID NO:1) and TK promoter upstream of the luciferase reporter cDNA, is transfected with a plasmid constitutively expressing human androgen receptor (AR) using viral CMV promoter. The reporter plasmid containing two copies of GRE (glucocorticoid response element 5'TGTACAGGATGTTCT$^3$') (SEQ ID NO:2) and TK promoter upstream of the luciferase reporter cDNA, is transfected with a plasmid constitutively expressing either human glucocorticoid receptor (GR), human mineralocorticoid receptor (MR), or human progesterone receptor (PR), using viral CMV promoter. Cells are transfected in T150 cm$^2$ flasks in DMEM media with 5% charcoal-stripped Fetal Bovine Serum (FBS). After an overnight incubation, transfected cells are trypsinized, plated in 96 well dishes in DMEM media containing 5% charcoal-stripped FBS, incubated for 4 h and then exposed to various concentrations of test compounds ranging from about 0.01 nM to 10 µM. In the antagonist assays low concentrations of agonist for each respective receptor are added to the media (0.25 nM dexamethosone for GR, 0.3 nM of methyltrienolone for AR, 0.05 nM of progesterone for PR and 0.05 nM aldosterone for MR). After 24 h of incubations with compounds, cells are lysed and luciferase activity is determined. Data is fit to a 4 parameter-fit logistics to determine EC50 values. The % efficacy is determined versus maximum stimulation obtained with 100 nM methyltrienolone for AR assay, with 30 nM progesterone for PR assay, with 30 nM aldosterone for MR assay and with 100 nM dexametasone for GR assay. In antagonist assays a % inhibition is calculated versus response of agonist alone (0.25 nM dexamethosone for GR, 0.3 nM of methyltrienolone for AR, 0.05 nM of progesterone for PR and 0.05 nM aldosterone for MR).

C2C12 AR/ARE Reporter Assay:

As an indicator of agonist activity in muscle tissue, the C2C12 AR/ARE reporter assay is performed. Briefly, mouse myoblast C2C12 cells are co-transfected using FuGENE™. A reporter plasmid containing a GRE/ARE (glucocorticoid response element/androgen response element 5'TGTACAGGATGTTCT$^3$) (SEQ ID NO:3) and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 4% or 10% Fetal Bovine Serum (FBS). After a 5 hour incubation, transfected cells are trypsinized, plated in 96 well dishes in DMEM media containing 10% charcoal-stripped FBS, incubated for 2 h and then exposed to various concentrations of test compounds ranging from about 0.01 nM to 10 µM. After 48 h of incubations with compounds, cells are lysed and luciferase activity is determined using standard techniques. Data is fit to a 4 parameter-fit logistics to determine EC50 values. The % efficacy is determined versus maximum stimulation obtained with 10 nM methyltrienolone.

Functional assays of nuclear hormone receptor modulation similar to those described above can be readily designed by the ordinarily skilled artisan. Table I (see below) provides average EC50 and % Efficacy data in a C2C12 AR/ARE reporter assay essentially as described above for a representative sample of the exemplified compounds of the present invention.

In Vivo Mouse Model of Efficacy and Selectivity:

Male ICR mice (8 weeks old) are castrated according to approved procedures (Taconic, N.Y.) and allowed to waste for eight weeks. Age-matched sham-operated mice are also prepared. (Sham-operated mice are animals that have been exposed to the same surgical procedures as castrated animals except their testes are not removed.) Animals are housed in a temperature-controlled room (24° C.) with a reversed 12 hour light/dark cycle (dark 10:00/22:00) and water and food are available ad libitum.

In order to demonstrate in vivo efficacy, compounds of the present invention are administered daily by oral gavage or subcutaneous injection to the castrated sixteen week old mice (body weight about 48-50 g). Test compounds are administered to the animals using conventional vehicles. For example, for oral dosing 1% Sodium Carboxymethylcellulose (CMC)+0.25% Tween 80 in sterile H$_2$O can be used for oral formulation and 6% Ethyl-alcohol (EtOH)+94% cyclodexitrane (CDX) can be used for subcutaneous injections. Castrated mice treated with Testosteron Enanthate (TE) (10 mg/kg/d) are used as a treatment positive control whereas castrated mice treated only with vehicle are used as treatment negative control. In addition, sham-operated mice treated with vehicle only are used as control for the surgical method.

Test animals are dosed over a two week timeframe, orally or subcutaneously, with, for example, 0.3, 1, 3, 10 or 30 mg/kg/day of a compound of the present invention. After the two-week treatment, as an indicator of activity the wet weight of the Levator Ani muscle in the test group is determined and compared to the weight in the castrated, vehicle-only control group. The percent efficacy is then calculated as follows:

(Wet weight in treatment group/Wet weight in control group)×100

As an indicator of tissue selective activity, the wet weight of the seminal vesicle from test animals is similarly compared to the weight of the seminal vesicles from the castrated, vehicle-only group. In addition, a comparison of the wet weight of the prostate glands from the drug-treated group, to the wet weight of the prostate glands removed from the castrated, vehicle-only group, may also be used as an indicator of tissue selective activity.

Table II (see below) provides % efficacy data for a select sample of exemplified compounds of the present invention in an animal model essentially as described above. Animal models of efficacy and selectivity similar to those described above can be readily designed and performed by the ordinarily skilled artisan, for example, Eisenberg and Gilbert, *J Pharmacol Exp Ther.* 1950, 99(1), 38-44, provides an alternative rat model that may be employed to show in vivo efficacy.)

In Vivo Models of Disorders Associated with Bone Loss:

To demonstrate that compounds of the present invention have the capacity to treat disorders associated with bone loss, such as osteoporosis or osteopenia, animal models well known to those in the art may be employed. Examples of such models are provided in Y. L. Ma et al., *Japanese Journal of Bone and Mineral Metabolism* 23 (Suppl.): 62-68 (2005); Y. L. Ma et al., *Endocrinology* 144: 2008-2015 (2003); and K. Hanada et al., *Biol. Pharm. Bull.* 26(11): 1563-1569 (2003). As will be appreciated by one of ordinary skill in the art, the animal model protocols described in the references above may be readily adapted for use in conjunction with the compounds and methods of the present invention.

The following preparations and examples further illustrate the invention and represent typical synthesis of the compounds of Formula I, including any novel compounds, as described generally above. The reagents and starting materials are readily available to, or may be readily synthesized by, one of ordinary skill in the art. For example, certain 2-aryl or 2-heterocyclic pyrrolidines may be obtained from commercial sources such as Lancaster, Windham, N.H., USA; Array Biopharma, Boulder, Colo., USA; or Beta Pharma, New Haven, Conn., USA. Where the synthesis of the compound is not explicitly stated, a reference to a previous Example or representative Scheme describing procedures for the synthesis of the compound is provided. It should be understood that the Preparations and Examples are set forth by way of illustration and not limitation, and that various modifications may be made by one of ordinary skill in the art.

Instrumental Analysis

Mass spectral analyses are conducted on one of the following: 1) ThermoFinnigen aQa using electrospray ionization (ESI); 2) Applied Biosystems API150EX mass spectrometer using atmospheric chemical ionization (APCI); 3) Micromass ZMD equipped with a Waters autosampler and using electrospray ionization (ESI); or 4) LCMS-APCI analysis is preformed on a Hewlett Packard LC/MSD using an Agilent Eclipse Zorbax SDB-C8, 5.0 μm column (4.6×150 mm). The flow rate is 0.5 mL/min. Elution system consists of an isocratic of 80:20 methanol/10 mM ammonium acetate buffer (pH 5.5) for 10 min. Proton nuclear magnetic resonance ($^1$H NMR) spectra are collected on a Bruker Avance 300 MHz or a Varian 400 MHz spectrometer. Chemical shift values are reported in parts per million (ppm) δ values, relative to TMS as the internal standard (bs, broad singlet; s, singlet; d, doublet; t, triplet; q, quartet). Melting points are determined on a MelTemp II, model 1001, and are uncorrected. All products are a racemic mixture of R and S stereoisomers unless indicated otherwise.

PREPARATIONS AND EXAMPLES

Preparation 1

2-Chloro-4-fluoro-3-methyl-benzonitrile

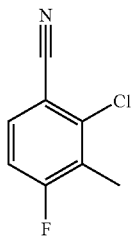

Cool a solution of diisopropylamine (80.6 mL, 0.575 mol) in THF (1 L) to about −5° C. using an ice water/MeOH bath. Add n-butyllithium (2.5 M in hexanes, 212 mL, 0.530 mol) dropwise over 1 h via a syringe pump (4 mL/min) while maintaining the reaction temperature between −5 to 0° C. during the addition.

Stir the lithium diisopropylamide (LDA) solution for 1 h at 0° C. and then transfer it via canula, over 1 h, to a −78° C. solution of 2-chloro-4-fluoro-benzonitrile (68.7 g, 0.442 mol) in THF (1 L). Allow the temperature of the reaction mixture to warm to about −65° C. during the initial addition of the LDA solution; however, keep the internal temperature below −70° C. during the remainder of the LDA addition. Keep the temperature of the resulting dark red-orange reaction mixture below −70° C. for 5 h and add iodomethane (251.2 g, 1.77 mol, 3 mL/min) at such a rate that the reaction temperature is maintained below −65° C. during the addition. Allow the reaction mixture to slowly warm overnight. After stirring for 14 h, the temperature of the reaction mixture is −5° C. Quench the reaction with saturated aqueous ammonium chloride (500 mL) and water (750 mL) and dilute with diethyl ether (about 2 L). Separate the layers and extract the aqueous layer with diethyl ether (about 1 L). Dry the combined organic layer (about 5.5 L) over MgSO$_4$, filter, and concentrate to afford the crude title compound as a red-brown oily solid (about 86.7 g). Subject the crude residue (dry loaded on silica gel using methylene chloride) to flash chromatography (silica gel (10× 30 cm), gradient of 99:1 to 93:7 hexane/EtOAc) to obtain the title compound (56.7 g, 76%) as a white solid. m.p. 63-65° C.; $^1$H NMR (300 MHz, CDCl$_3$): δ 7.54 (dd, J=8.6, 5.6 Hz, 1H), 7.08 (dd, J=8.6, 8.6 Hz, 1H), 2.36 (d, J=2.4 Hz, 3H).

Preparation 2

[4-(3-Methoxy-phenyl)-4-oxo-butyl]-carbamic acid tert-butyl ester

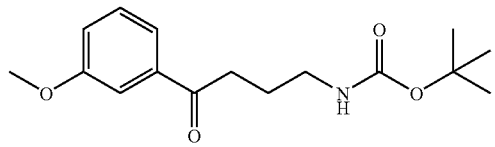

Add 3-methoxyphenylmagnesium bromide (1.0 M in tetrahydrofuran, 91.0 mL, 91.0 mmol) dropwise to 1-(tert-butoxycarbonyl)-2-pyrrolidinone (11.9 mL, 70.0 mmol) in tetrahydrofuran (230 mL) at −40° C. After stirring at −40° C. for one hour, warm to 0° C. for 2 h before quenching with 2 M hydrochloric acid (70 mL). Dilute with methylene chloride (250 mL), separate the layers, and extract the aqueous layer with methylene chloride (2×200 mL). Dry the combined organic layers over magnesium sulfate, filter, and concentrate under reduced pressure to obtain the title compound (23.20 g, >100%). MS (APCI+): 194 [C$_{16}$H$_{23}$NO$_4$—C$_5$H$_8$O$_2$+H]$^+$; $^1$H NMR (300 MHz, CDCl$_3$): δ 7.55-7.47 (m, 2H), 7.39-7.33 (m, 1H), 7.12-7.08 (m, 1H), 4.66 (bs, 1H), 3.85 (s, 3H), 3.29-3.18 (m, 2H), 3.01 (t, J=7.1 Hz, 2H), 1.93 (quintet, J=7.0 Hz, 2H), 1.42 (s, 9H).

Preparation 3

[4-(3-Methylsulfanyl-phenyl)-4-oxo-butyl]-carbamic acid tert-butyl ester

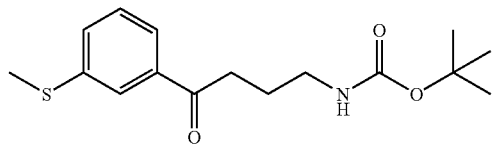

Cool a solution of 3-bromothioanisole (10.68 g, 52.6 mmol) in tetrahydrofuran (250 mL) to −78° C., and add n-butyllithium (2.5 M in hexanes, 25.9 mL, 64.8 mmol) over 25 min. Stir the reaction at −78° C. for 1.25 h, then slowly add a solution of 1-(tert-butoxycarbonyl)-2-pyrrolidinone (7.50 g, 40.5 mmol) in tetrahydrofuran (100 mL). Stir the reaction for 2 h at −78° C., then add saturated aqueous ammonium chloride (100 mL). Upon warming to room temperature, add water (200 mL), and extract the reaction with dichloromethane (3×300 mL). Combine the organic extracts and dry over magnesium sulfate, filter, and evaporate under reduced pressure to afford a crude mixture (14.91 g). Purify the crude mixture by flash chromatography (330 g RediSep silica gel column, gradient from 0:100 to 30:70 ethyl acetate:hexanes) to provide slightly impure product (10.34 g, 83%), which is used without further purification. MS (APCI+): 210 $[C_{16}H_{23}NO_3S—C_5H_8O_2+H]^+$; $^1$H NMR (300 MHz, CDCl$_3$): δ 7.81-7.82 (m, 1H), 7.67-7.71 (m, 1H), 7.41-7.45 (m, 1H), 7.34-7.39 (m, 1H), 4.64 (br s, 1H), 3.17-3.26 (m, 2H), 3.00 (t, J=7.1 Hz, 2H), 2.52 (s, 3H), 1.93 (quintet, J=7.0 Hz, 2H), 1.42 (s, 9H).

Preparation 4

(4-Oxo-4-pyrimidin-5-yl-butyl)-carbamic acid tert-butyl ester

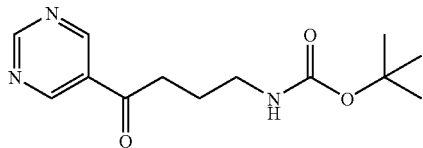

Cool a solution of 5-bromopyrimidine (7.63 g, 48.0 mmol) in tetrahydrofuran (375 mL) to −100° C., and add slowly n-butyllithium (2.5 M in hexanes, 17.8 mL, 44.5 mmol), keeping the temperature below −90° C. Stir the reaction for 30 min at −100° C. Cool a solution of 1-(tert-butoxycarbonyl)-2-pyrrolidinone (8.08 g, 43.6 mmol) in tetrahydrofuran (100 mL) to −78° C. and add to the reaction mixture with a cannula. Stir the reaction at −100° C. for 30 min, then add a 2 M solution of hydrogen chloride in diethyl ether (25 mL, 50 mmol). Allow the reaction to warm to room temperature and add dichloromethane (500 mL) and water (500 mL). Separate the layers and extract the aqueous layer with dichloromethane (2×250 mL). Combine the organic portions and wash with brine (400 mL), dry over magnesium sulfate, filter, and evaporate under reduced pressure to afford a crude mixture (10.98 g). Purify by flash chromatography (two stacked 120 g RediSep silica gel columns, 0:100 to 30:70 gradient of [90:10:1 dichloromethane:methanol:concentrated ammonium hydroxide]:dichloromethane) to provide an impure mixture containing the product (5.35 g, ~35%) which is used without further purification. MS (APCI+): 148 $[C_{13}H_{19}N_3O_3—C_5H_8O_2—H_2O+H]^+$; $^1$H NMR (300 MHz, CDCl$_3$): δ 9.36 (s, 1H), 9.22 (s, 2H), 4.63 (br s, 1H), 3.19-3.29 (m, 2H), 3.04 (t, J=7.0 Hz, 2H), 1.97 (quintet, J=6.8 Hz, 2H), 1.41 (s, 9H).

Prepare the intermediates in the table below, Preparations 5 to 7, by essentially following the procedures as described in Preparation 2.

| Prep. No. | Structure | |
|---|---|---|
| 5 | (1,3-benzodioxol-5-yl ketone with Boc-aminobutyl chain) | MS (ESI+): 208 (M − C$_5$H$_8$O$_2$ + H)$^+$; $^1$H NMR (300 MHz, CDCl$_3$): δ 7.55 (dd, J=1.7, 8.2 Hz, 1H), 7.42 (d, J=1.7 Hz, 1H), 6.84 (d, J=8.2 Hz, 1H), 6.04 (s, 2H), 4.68 (br s, 1H), 3.17-3.27 (m, 2H), 2.94 (t, J=7.2 Hz, 2H), 1.92 (quintet, J=7.0 Hz, 2H), 1.43 (s, 9H). |
| 6 | (4-methylthiophenyl ketone with Boc-aminobutyl chain) | MS (APCI+): 210 (M − C$_5$H$_8$O$_2$ + H)$^+$; $^1$H NMR (300 MHz, CDCl$_3$): δ 7.84-7.88 (m, 2H), 7.22-7.28 (m, 2H), 4.68 (br s, 1H), 3.17-3.26 (m, 2H), 2.97 (t, J=7.1 Hz, 2H), 2.52 (s, 3H), 1.92 (quintet, J=7.0 Hz, 2H), 1.42 (s, 9H). |
| 7 | (2-methoxyphenyl ketone with Boc-aminobutyl chain) | $^1$H NMR (300 MHz, CDCl$_3$): δ 7.67 (dd, J=1.8, 7.6 Hz, 1H), 7.42-7.48 (m, 1H), 7.01 (dd, J=0.9, 7.5 Hz, 1H), 6.96 (d, J=8.0 Hz, 1H), 4.66-4.70 (m, 1H), 3.90 (s, 3H), 3.15-3.25 (m, 2H), 2.97-3.05 (m, 2H), 1.88 (quintet, J=7.1 Hz, 2H), 1.43 (s, 9H). |

Preparation 8

5-(3-Methoxy-phenyl)-3,4-dihydro-2H-pyrrole

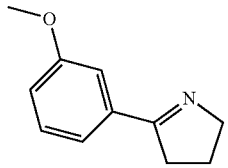

Add trifluoroacetic acid (49.8 mL, 670 mmol) to [4-(3-methoxy-phenyl)-4-oxo-butyl]-carbamic acid tert-butyl ester (22.21 g, 67 mmol) with ice/water cooling. After stirring at 0° C. for 3.5 h, adjust the reaction to pH 10 with 50% sodium hydroxide. Extract the reaction mixture with ether (5×100 mL), dry the combined organic layers over magnesium sulfate, filter, and concentrate under reduced pressure to obtain the crude product (15.43 g). Purify by flash chromatography [silica gel, 330 g, 0 to 30% gradient of (90:10:1 methylene chloride/methanol/concentrated ammonium hydroxide) in methylene chloride] to obtain the title compound (10.76 g, 88% for two steps). MS (APCI+): 176 $[C_{11}H_{13}NO+H]^+$; $^1$H NMR (300 MHz, CDCl$_3$): δ 7.46-7.45 (m, 1H), 7.37-7.27 (m, 2H), 6.99-6.95 (m, 1H), 4.09-4.03 (m, 2H), 3.84 (s, 3H), 2.96-2.89 (m, 2H), 2.08-1.97 (m, 2H).

Prepare the intermediates in the table below, Preparations 9 to 13, by essentially following the procedures as described in Preparation 8.

Preparation 14

2-(3-Methoxy-phenyl)-pyrrolidine

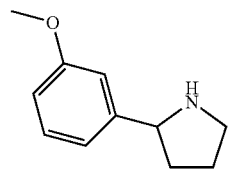

To a solution of 5-(3-methoxy-phenyl)-3,4-dihydro-2H-pyrrole (10.73 g, 61.2 mmol) in ethanol (306 mL) at 0° C. add sodium cyanoborohydride (5.77 g, 91.9 mmol), followed by acetic acid (5.26 mL, 91.9 mmol). After stirring at 0° C. for 30 min, warm to room temperature. After 16 hours the reaction is approximately 50% complete. Add more sodium cyanoborohydride (5.77 g, 91.9 mmol) and acetic acid (5.26 mL, 91.9 mmol) and stir an additional 5 hours. Add saturated aqueous sodium bicarbonate (500 mL), extract with methylene chloride (3×500 mL), dry the combined organic layers over magnesium sulfate, filter, and concentrate under reduced pressure to obtain a crude mixture (11.50 g). Purify the material by flash chromatography [silica gel, 330 g, 0 to 100% gradient of (90:10:1 methylene chloride/methanol/concentrated ammonium hydroxide) in methylene chloride] to obtain 7.06 g. Dissolve this crude material in ethyl acetate (300 mL) and extract with 2 M hydrochloric acid (2×150 mL). Separate the layers, and adjust the aqueous layer to pH 13 with aqueous

| Prep | Structure | Physical Data |
|------|-----------|---------------|
| 9 | 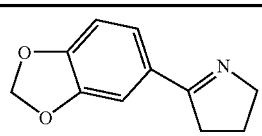 | MS (APCI+): 190 (M + H)$^+$; $^1$H NMR (300 MHz, CDCl$_3$): δ 7.42 (d, J=1.6 Hz, 1H), 7.27 (dd, J=1.6, 8.1 Hz, 1H), 6.80 (d, J=8.1 Hz, 1H), 6.00 (s, 2H), 3.99-4.06 (m, 2H), 2.82-2.92 (m, 2H), 1.95-2.07 (m, 2H). |
| 10 | 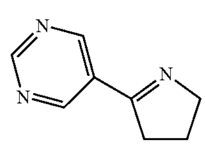 | MS (APCI+): 148 (M + H)$^+$; $^1$H NMR (300 MHz, CDCl$_3$): δ 9.25 (s, 1H), 9.14 (s, 2H), 4.09-4.15 (m, 2H), 2.92-2.99 (m, 2H), 2.05-2.15 (m, 2H). |
| 11 | 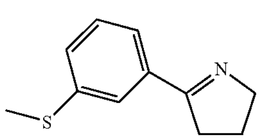 | $^1$H NMR (300 MHz, CDCl$_3$): δ 7.74-7.80 (m, 1H), 7.52-7.59 (m, 1H), 7.28-7.33 (m, 2H), 4.00-4.10 (m, 2H), 2.86-2.96 (m, 2H), 2.51 (s, 3H), 1.98-2.09 (m, 2H). |
| 12 | 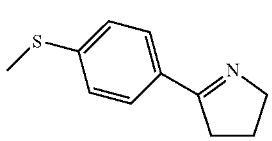 | MS (APCI+): 192 (M + H)$^+$; $^1$H NMR (300 MHz, CDCl$_3$): δ 7.70-7.77 (m, 2H), 7.24-7.26 (m, 2H), 4.02-4.10 (m, 2H), 2.89-2.96 (m, 2H), 2.51 (s, 3H), 1.98-2.09 (m, 2H). |
| 13 | | MS (APCI+): 176 (M + H)$^+$; $^1$H NMR (300 MHz, CDCl$_3$): δ 7.72-7.75 (m, 1H), 7.32-7.38 (m, 1H), 6.90-6.99 (m, 2H), 3.94-4.00 (m, 2H), 3.85 (s, 3H), 2.96-3.03 (m, 2H), 1.92-2.02 (m, 2H). | sodium hydroxide, then extract with ethyl acetate multiple times. Dry the combined organic layers over magnesium sulfate, filter, and concentrate under reduced pressure to obtain 6.03 g. Dissolve in methylene chloride (400 mL) and extract with 2 M hydrochloric acid (3×100 mL). Adjust the combined aqueous layers to pH 13, then extract with methylene chloride (3×150 mL). Separate the layers, and dry the combined organic layers over magnesium sulfate, filter, and concentrate under reduced pressure to obtain the title compound (4.12 g, 38%). MS (ESI+): 178 [$C_{11}H_{15}NO+H$]$^+$; $^1$H NMR (300 MHz, CDCl$_3$): δ 7.26-7.20 (m, 1H), 6.95-6.93 (m, 2H), 6.79-6.75 (m, 1H), 3.80 (s, 3H), 4.09 (t, J=7.7 Hz, 1H), 3.24-3.16 (m, 1H), 3.04-2.96 (m, 1H), 2.19 (s, 1H), 2.23-2.12 (m, 1H), 1.98-1.76 (m, 2H), 1.72-1.60 (m, 1H).

Prepare the intermediates in the table below, Preparations 15 to 19, by essentially following the procedures as described in Preparation 14.

rahydrofuran (60 mL). After stirring for 45 min, add methyllithium (1.6 M in diethyl ether, 10.70 mL, 17.10 mmol) dropwise over 10 min. After stirring the bright yellow reaction mixture for 2.5 h, warm the reaction mixture slowly to 0° C. After 1.5 h replace the dry ice/acetone cooling bath with an ice bath. After 15 min, quench the reaction using water (50 mL) and saturated aqueous ammonium chloride (50 mL) and adjust the pH to about 11-12 using aqueous 2 M sodium hydroxide. Extract the aqueous layer with 9:1 methylene chloride/chloroform (3×200 mL) and dry the combined organic layers over magnesium sulfate, filter, and concentrate under reduced pressure to obtain an orange oil. Redissolve the crude oil in methylene chloride (200 mL) and add aqueous 2 M hydrochloric acid (200 mL). Separate the layers and extract the aqueous layer with additional methylene chloride (100 mL) and discard the combined organic layers. Adjust the resulting aqueous layer to a pH of 14 using aqueous 2 M

| Prep | Structure | Physical Data |
|---|---|---|
| 15 | 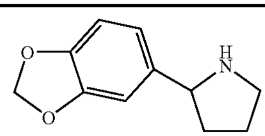 | MS (ESI+) 192.5 (M + 1)$^+$; $^1$H NMR (300 MHz, CDCl$_3$): δ 7.22-7.31 (m, 2H), 7.13 (d, 2H), 4.09 (t, 1H), 3.21 (m, 1H), 3.02 (m, 1H), 2.19 (m, 1H), 2.48 (s, 3H), 1.89 (m, 2H), 1.89 (broad s, 1H, NH), 1.64 (m, 1H). |
| 16 | 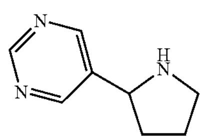 | MS (ESI+): 150.13 (M + 1)$^+$; $^1$H NMR (300 MHz, CDCl$_3$): δ 9.10 (s, 1H), 8.74 (s, 2H), 4.20 (t, 1H), 3.19 (m, 1H), 3.09 (m, 1H), 2.28 (m, 1H), 1.96 (broad s, 1H, NH), 1.94 (m, 2H), 1.68 (m, 1H). |
| 17 | 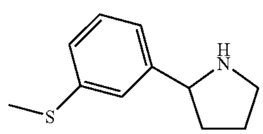 | MS (ESI+): 194.3 (M + 1)$^+$; $^1$H NMR (300 MHz, CDCl$_3$): δ 7.22-7.31 (m, 2H), 7.13 (d, 2H), 4.09 (t, 1H), 3.21 (m, 1H), 3.02 (m, 1H), 2.48 (s, 3H), 2.19 (m, 1H), 1.89 (m, 2H), 1.89 (broad s, 1H, NH), 1.64 (m, 1H). |
| 18 | 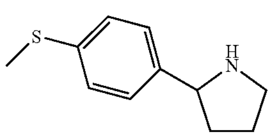 | MS (ESI+): 194.17 (M + 1)$^+$; $^1$H NMR (300 MHz, CDCl$_3$): δ 7.28 (d, 1H), 7.22 (d, 2H), 4.08 (t, 1H), 3.19 (m, 1H), 3.01 (m, 1H), 2.47 (s, 3H), 2.17 (m, 1H), 1.89 (m, 2H), 1.89 (broad s, 1H, NH), 1.64 (m, 1H). |
| 19 | 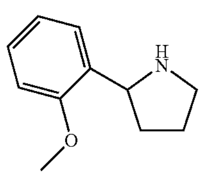 | MS (ESI+): 178.16 (M + 1)$^+$; $^1$H NMR (300 MHz, CDCl$_3$): δ 7.22-7.31 (m, 2H), 7.13 (d, 2H), 4.09 (t, 1H), 3.21 (m, 1H), 3.02 (m, 1H), 2.48 (s, 3H), 2.19 (m, 1H), 1.89 (m, 2H), 1.89 (broad s, 1H, NH), 1.64 (m, 1H). |

Preparation 20

2-(3-Methoxy-phenyl)-2-methyl-pyrrolidine

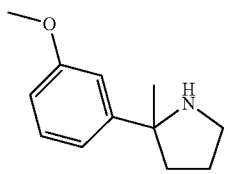

Add boron trifluoride diethyl etherate (1.34 g, 9.42 mmol) dropwise over 5 min to a −78° C. solution of 5-(3-methoxyphenyl)-3,4-dihydro-2H-pyrrole (1.50 g, 8.56 mmol) in tetsodium hydroxide (about 250 mL), extract with 1:1 methylene chloride/chloroform (2×250 mL), dry the combined organic layers over magnesium sulfate, filter, and concentrate under reduced pressure to obtain an orange oil (1.30 g). Purify the oil by flash chromatography eluting with a gradient of methylene chloride/90:10:1 methylene chloride/methanol/concentrated ammonium hydroxide (4:1 to 1:1) to obtain the title compound (650 mg, 40%) as a light yellow oil. MS (APCI+): 192 [$C_{12}H_{17}NO+H$]$^+$; $^1$H NMR (300 MHz, CDCl$_3$): δ 7.24 (symmetrical m, 1H), 7.09-7.03 (m, 2H), 6.75 (ddd, J=8.1, 2.6, 0.9 Hz, 1H), 3.81 (s, 3H), 3.16-2.94 (symmetrical m, 2H), 2.14-2.01 (m, 1H), 1.94-1.67 (m, 4H), 1.42 (s, 3H).

Preparation 21

2-Benzo[1,3]dioxol-5-yl-2-methyl-pyrrolidine

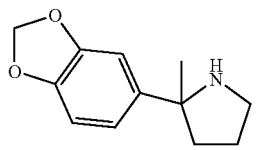

To a −78° C. solution of 5-benzo[1,3]dioxol-5-yl-3,4-dihydro-2H-pyrrole (1.67 g, 8.83 mmol) in THF (60 mL) add boron trifluoride diethyl etherate (1.22 mL, 9.71 mmol) dropwise over 5 min. Stir the resulting cloudy reaction mixture at this temperature for 40 min, and then add methyllithium (1.6 M in diethyl ether, 27.5 mL, 44.1 mmol) dropwise via a syringe pump (about 1.1 mL/minute) over 20 min. Maintain the reaction temperature at −78° C. for 2.5 h and then warm to 0° C. over 1.5 h. Quench the reaction by the addition of water (50 mL) and saturated aqueous ammonium chloride (50 mL), then adjust the mixture to a pH of about 11-12 using aqueous 2 M NaOH, and extract with 9:1 methylene chloride/chloroform (3×330 mL). Dry the combined organic layer (MgSO$_4$), filter and concentrate under reduced pressure to obtain a crude brown oil (~2.6 g). Subject the crude residue (dry loaded on silica gel using CH$_2$Cl$_2$) to flash chromatography (120 g silica gel, gradient from 80:20 to 50:50 CH$_2$Cl$_2$/[90:10:1 CH$_2$Cl$_2$/MeOH/NH$_4$OH]) to afford pure title compound (910 mg, 50%, >95% purity by $^1$H NMR) and impure title compound (358 mg, 20%, ~85% purity by $^1$H NMR) as light brown oils. MS (ESI+): 206 (M+1)$^+$; $^1$H NMR (300 MHz, CDCl$_3$): δ 7.01 (d, J=1.8 Hz, 1H), 6.93 (dd, J=8.1, 1.8 Hz, 1H), 6.75 (d, J=8.1 Hz, 1H), 5.92 (s, 2H), 3.12-3.05 (m, 1H), 3.00-2.92 (m, 1H), 2.06-2.00 (m, 1H), 1.88-1.69 (m, 4H), 1.40 (s, 3H).

Example 1

2-Chloro-3-methyl-4-(2-phenyl-pyrrolidin-1-yl)-benzonitrile

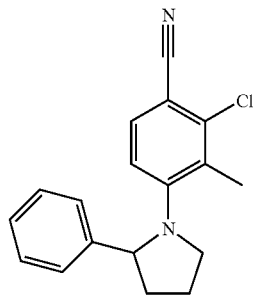

Heat 2-chloro-4-fluoro-3-methyl-benzonitrile (144 mg, 0.85 mmol) and 2-phenyl-pyrrolidine (0.15 g, 1.02 mmol, 1.20 equivalents) in N-methylmorpholine (0.11 ml, 1.02 mmol, 1.20 equivalents) at 150° C. overnight. Allow the reaction mixture to cool to room temperature, dilute with dichloromethane (1 ml), load on silica, and purify by chromatography (12 g silica gel, 0 to 100% ethyl acetate/hexanes over 20 minutes) to obtain 150 mg of an oily residue. Recrystallize from ethyl acetate/hexanes to obtain the title compound (92 mg, 37%). LCMS (APCI+): 297.0 (M+1)$^+$; $^1$H NMR (400 MHz, CDCl$_3$): δ 7.25 (s, 2H), 7.19 (m, 2H), 6.65 (d, 1H), 4.70 (m, 1H), 4.06 (m, 1H), 3.18 (m, 1H), 2.44 (m, 1H), 2.43 (s, 3H), 2.12 (m, 1H), 1.94 (m, 2H).

Prepare Examples 2 to 20, in the table below, by essentially following the procedures as described in Example 1 above. Use the appropriate pyrrolidine as indicated and 2-chloro-4-fluoro-3-methyl-benzonitrile (Preparation 1), 2-chloro-4-fluorobenzonitrile, or 4-fluoro-2-(trifluoromethyl)benzonitrile.

| Ex | Source of 2-aryl or 2-heterocyclic pyrrolidine | Product Structure | Physical Data |
|---|---|---|---|
| 2 | Elslager, E. F., Johnson J. L., Werbel, L. M. *J. Med. Chem.* (1981), 24(2), 140-5. | | LCMS (APCI+): 331.0 (M + 1)$^+$; $^1$H NMR (400 MHz, CDCl$_3$): δ 7.18-7.22 (m, 5H), 6.63 (d, 1H), 4.68 (m, 1H), 4.06 (m, 1H), 3.18 (m, 1H), 2.46 (m, 1H), 2.42 (s, 3H), 2.12 (m, 1H), 1.94 (m, 2H). |

-continued

| Ex | Source of 2-aryl or 2-heterocyclic pyrrolidine | Product Structure | Physical Data |
|---|---|---|---|
| 3 | Commercially available | | LCMS (APCI+): 315.0 (M + 1)+; $^1$H NMR (400 MHz, CDCl$_3$): δ 7.21 (m, 3H), 6.95 (t, 2H), 6.61 (d, 1H), 4.68 (m, 1H), 4.03 (m, 1H), 3.17 (m, 1H), 2.44 (m, 1H), 2.42 (s, 3H), 2.12 (m, 1H), 1.81-1.97 (m, 2H). |
| 4 | Anderson, A. G., Jr.; Wills, M. T. *J. Org. Chem.* (1967), 32(10), 3241-3. | | LCMS (APCI+): 325.0 (M + 1)+; $^1$H NMR (400 MHz, CDCl$_3$): δ 7.18-7.26 (m, 6H), 6.65 (d, 1H), 4.93 (dd, 1H), 3.82 (d, 1H), 2.94 (d, 1H), 2.42 (s, 3H), 2.17 (17, 1H), 1.78 (t, 1H), 1.20 (s, 3H), 1.05 (s, 3H). |
| 5 | Preparation 14 | | LCMS (APCI+): 327.0 (M + 1)+; $^1$H NMR (400 MHz, CDCl$_3$): δ 7.18-7.21 (m, 2H), 6.84 (d, 1H), 6.79 (s, 1H), 6.72 (dd, 1H), 6.65 (d, 1H), 4.66 (m, 1H), 4.01 (m, 1H), 3.75 (s, 3H), 3.15 (m, 1H), 2.45 (m, 1H), 2.43 (s, 3H), 2.09 (m, 1H), 1.84-1.97 (m, 2H). |
| 6 | Preparation 19 | | MS (ESI+): 327.2 (M + 1)+; $^1$H NMR (400 MHz, CDCl$_3$): δ 7.15-7.20 (m, 2H), 6.79-6.83 (m, 2H), 6.60 (d, 1H), 5.12 (m, 1H), 4.03 (m, 1H), 3.87 (s, 3H), 3.19 (t, 1H), 2.52 (m, 1H), 2.44 (s, 3H), 2.09 (m, 1H), 1.77-1.99 (m, 2H). |

-continued

| Ex | Source of 2-aryl or 2-heterocyclic pyrrolidine | Product Structure | Physical Data |
|---|---|---|---|
| 7 | Commercially available | | MS (ESI+): 327.2 (M + 1)+; $^1$H NMR (400 MHz, CDCl$_3$): δ 7.20 (d, 1H), 7.17 (d, 2H), 6.79 (d, 2H), 6.62 (d, 1H), 4.63 (m, 1H), 4.01 (m, 1H), 3.75 (s, 3H), 3.15 (t, 1H), 2.42 (s, 3H), 2.41 (m, 1H), 2.09 (m, 1H), 1.82-1.95 (m, 2H). |
| 8 | Commercially available | | LCMS (APCI+): 365.0 (M + 1)+; $^1$H NMR (400 MHz, CDCl$_3$): δ 7.63 (d, 1H), 7.58 (d, 1H), 7.41 (t, 1H), 7.28 (t, 1H), 7.19 (d, 1H), 6.67 (d, 1H), 5.05 (dd, 1H), 4.05 (q, 1H), 3.75 (s, 3H), 3.13 (dt, 1H), 2.58 (m, 1H), 2.47 (s, 3H), 2.11 (m, 1H), 1.97-2.04 (m, 1H), 1.75-1.82 (m, 1H). |
| 9 | Commercially available | | MS (ESI+): 298.2 (M + 1)+; $^1$H NMR (400 MHz, CDCl$_3$): δ 8.54 (d, 1H), 8.44 (d, 1H), 7.53 (d, 1H), 7.17-7.22 (m, 1H), 6.62 (d, 1H), 4.74 (dd, 1H), 4.02 (q, 1H), 3.14 (t, 1H), 2.48 (m, 1H), 2.41 (s, 3H), 2.15 (m, 1H), 1.84-2.01 (m, 2H). |
| 10 | Commercially available | | $^1$H NMR (400 MHz, CDCl$_3$): δ 8.51 (d, 1H), 7.54 (t, 1H), 7.19 (m, 2H), 7.12 (m, 1H), 6.71 (d, 1H), 4.86 (m, 1H), 4.05 (q, 1H), 3.20 (t, 1H), 2.60 (m, 1H), 2.42 (s, 3H), 2.14 (m, 1H), 1.88-2.02 (m, 2H), |

-continued

| Ex | Source of 2-aryl or 2-heterocyclic pyrrolidine | Product Structure | Physical Data |
|---|---|---|---|
| 11 | Commercially available | | MS (ESI+): 298.2 (M + 1)⁺; ¹H NMR (400 MHz, CDCl₃): δ 8.51 (d, 2H), 7.22-7.30 (m, 4H), 6.58 (d, 1H), 4.77 (dd, 1H), 4.02 (q, 1H), 3.18 (t, 1H), 2.52 (m, 1H), 2.43 (s, 3H), 2.15 (m, 1H), 1.94-2.06 (m, 1H), 1.82-1.92 (m, 1H). |
| 12 | Preparation 15 | | LCMS (APCI+): 341.0 (M + 1)⁺; ¹H NMR (400 MHz, CDCl₃): δ 7.22 (d, 1H), 6.68-6.74 (m, 4H), 5.90 (d, 2H), 4.61 (m, 1H), 4.03 (m, 1H), 3.75 (s, 3H), 3.15 (t, 1H), 2.42 (s, 3H), 2.39 (m, 1H), 2.09 (m, 1H), 1.86-1.98 (m, 2H). |
| 13 | Preparation 17 | | LCMS (APCI+): 343.0 (M + 1)⁺; ¹H NMR (400 MHz, CDCl₃): δ 7.13-7.21 (m, 2H), 7.05 (d, 1H), 7.00 (d, 1H), 6.64 (d, 1H), 4.68 (m, 1H), 4.01 (m, 1H), 3.14 (m, 1H), 2.44 (m, 1H), 2.42 (s, 3H), 2.41 (s, 3H), 2.08 (m, 1H), 1.84-1.97 (m, 2H). |
| 14 | Preparation 18 | | LCMS (APCI+): 343.0 (M + 1)⁺; ¹H NMR (400 MHz, CDCl₃): δ 7.13-7.21 (m, 5H), 6.62 (d, 1H), 4.65 (m, 1H), 4.01 (m, 1H), 3.13 (m, 1H), 2.42 (m, 1H), 2.41 (s, 6H), 2.09 (m, 1H), 1.82-1.97 (m, 2H) |
| 15 | Preparation 16 | | LCMS (APCI+): 299.0 (M + 1)⁺; ¹H NMR (400 MHz, CD₃OD): δ 8.77 (s, 2H), 8.98 (s, 1H), 7.36 (d, 1H), 6.89 (d, 1H), 4.94 (m, 1H), 4.09 (m, 1H), 3.18 (m, 1H), 2.58 (m, 1H), 2.15 (m, 1H), 2.46 (s, 3H), 1.90-2.09 (m, 2H). |

| Ex | Source of 2-aryl or 2-heterocyclic pyrrolidine | Product Structure | Physical Data |
|----|---|---|---|
| 16 | Commercially available | | LCMS (APCI+): 284.0 (M + 1)$^+$; $^1$H NMR (400 MHz, CDCl$_3$): δ 8.54 (broad s, 1H), 8.44 (broad s, 1H), 7.41 (d, 1H), 7.33 (d, 1H), 7.26 (m, 1H), 6.51 (s, 1H), 6.32 (d, 1H), 4.85 (d, 1H), 3.73 (m, 1H), 3.47 (m, 1H), 2.48 (m, 1H), 1.96-2.15 (m, 2H). |
| 17 | Preparation 21 | | LCMS (APCI+): 341.0 (M + 1)$^+$; $^1$H NMR (400 MHz, CDCl$_3$): δ 7.21 (d, 1H), 6.75 (d, 1H), 6.66 (d, 1H), 6.63 (s, 1H), 6.48 (s, 1H), 6.24 (d, 1H), 5.94 (s, 2H), 3.62 (t, 1H), 2.15 (m, 2H), 2.02 (m, 2H), 1.76 (s, 3H). |
| 18 | Preparation 20 | | LCMS (APCI+): 327.0 (M + 1)$^+$; $^1$H NMR (400 MHz, CD$_3$OD): δ 7.29 (d, 1H), 7.25 (t, 1H), 6.82 (m, 2H), 6.76 (s, 1H), 6.51 (s, 1H), 6.37 (d, 1H), 3.74 (s, 3H), 3.69 (t, 2H), 2.00-2.27 (m, 4H), 1.80 (s, 3H). |
| 19 | Preparation 15 | | LCMS (APCI+): 361.2 (M + 1)$^+$; $^1$H NMR (400 MHz, CDCl$_3$): δ 7.44 (d, 1H), 6.78 (s, 1H), 6.75 (d, 1H), 6.59 (d, 2H), 6.52 (d, 1H), 5.94 (d, 2H), 4.73 (d, 1H), 3.72 (m, 1H), 3.48 (q, 1H), 2.42 (m, 1H), 2.02-2.16 (m, 2H), 1.97 (m, 1H). |
| 20 | Preparation 21 | | LCMS (APCI+): 375.2 (M + 1)$^+$; $^1$H NMR (400 MHz, CDCl$_3$): δ 7.39 (d, 1H), 6.75 (d, 1H), 6.74 (s, 1H), 6.67 (d, 1H), 6.65 (s, 1H), 6.45 (d, 1H), 5.94 (s, 2H), 3.68 (t, 1H), 2.18 (m, 2H), 2.04 (m, 2H), 1.76 (s, 3H). |

Example 21

2-Chloro-4-[2-(3-methanesulfonyl-phenyl)-pyrrolidin-1-yl]-3-methyl-benzonitrile

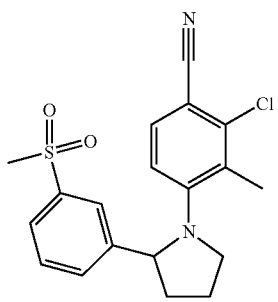

To a solution of 2-chloro-3-methyl-4-[2-(4-methylsulfanyl-phenyl)-pyrrolidin-1-yl]-benzonitrile (167 mg, 0.49 mmol) in methanol (5 mL)/tetrahydrofuran (5 mL) at room temperature add oxone (1.50 g, 2.44 mmol, 5.00 equivalents) in water (5 mL) and stir the reaction mixture at room temperature overnight. Dilute the mixture with ethyl acetate, wash with water (2×), dry the organic phase over anhydrous sodium sulfate, filter, and concentrate under reduced pressure to obtain a yellow solid (200 mg). Subject to flash chromatography (12 g silica gel, 0 to 100% ethyl acetate/hexanes gradient over 20 minutes) to obtain the pure title compound (119 mg, 65%). LCMS (APCI+): 375.0 (M+1)$^+$; $^1$H NMR (400 MHz, CDCl$_3$): δ 7.84 (s, 1H), 7.76 (d, 1H), 7.53 (d, 1H), 7.46 (t, 1H), 7.13 7.20 (d, 1H), 6.63 (d, 1H), 4.81 (m, 1H), 4.03 (m, 1H), 3.15 (m, 1H), 2.99 (s, 3H), 2.51 (m, 1H), 2.42 (s, 3H), 2.14 (m, 1H), 1.83-2.01 (m, 2H).

Preparation 22

1-Phenyl-hexane-1,4-diol

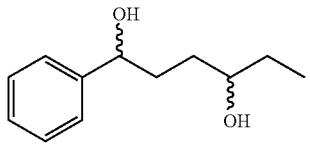

Dissolve 5-phenyl-dihydro-furan-2-one (10.38 g, 64 mmol) in THF (200 mL) in a dry flask that has been purged with nitrogen. Cool the flask to −78° C. and add diisobutylaluminum hydride (64 mL, 64 mmol, 1.0M in heptane, 1 eq.) slowly.

After one hour, add ethylmagnesium bromide (64 mL, 192 mmol, 1.0M in THF) and stir for 17 h while allowing the reaction to warm to room temperature. Cool the reaction mixture to 0° C. and quench with 1.0N HCl. Add brine, and extract with Et$_2$O, Separate and dry the organic portion over Na$_2$SO$_4$, filter, and concentrate. Purify using silica gel chromatography, using 20% EtOAc/hexanes to obtain 9.2 g (74%) of the title compound as a colorless oil. MS (ESI−): 193 (M−1)$^-$.

Preparation 23

Methanesulfonic acid 4-methanesulfonyloxy-1-phenyl-hexyl ester

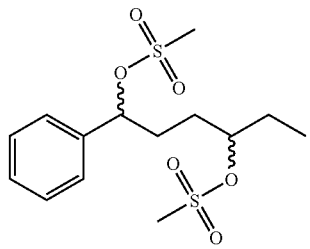

Stir methanesulfonyl chloride (2.94 g, 25.7 mmol) in dichloromethane (40 mL) in a flask that has been purged with nitrogen. Cool the mixture to −20° C. and add 1-phenyl-hexane-1,4-diol (2.0 g, 10.3 mmol) dissolved in dichloromethane (5 mL), and triethylamine (3.13 g, 30.9 mmol). After 2 h of stirring at −20° C., quench with saturated aqueous NH$_4$Cl solution and concentrate to a quarter of the volume. Dilute with EtOAc, and wash with saturated NaHCO$_3$ solution, water, and brine. Dry the organic portion over Na$_2$SO$_4$, filter, and concentrate to obtain 3.0 g (83%) of the title compound. Use with no further purification. $^1$H NMR (400 MHz, CD$_3$OD): δ 7.37-7.24 (m, 5H), 4.69-4.59 (m, 1H), 4.21-4.14 (m, 1H), 3.01 (s, 3H), 2.73 (s, 3H), 1.91-1.55 (m, 6H), 0.96-0.88 (m, 3H).

Example 22

2-Chloro-4-(2-ethyl-5-phenyl-pyrrolidin-1-yl)-benzonitrile

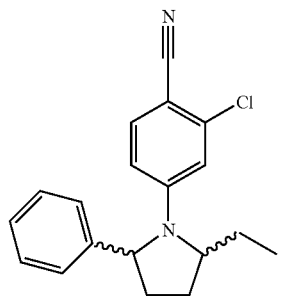

Dissolve methanesulfonic acid 4-methanesulfonyloxy-1-phenyl-hexyl ester (1.01 g, 2.88 mmol) in toluene (20 mL) in a reaction tube. Add 4-amino-2-chlorobenzonitrile (1.10 g, 7.2 mmol), purge with nitrogen and cap. Heat the reaction in a 120° C. oil bath for 17 h. Cool, concentrate, and purify by silica gel chromatography using 5-30% EtOAc/hexanes to obtain 0.22 g (25%0 of the title compound as a clear oil. MS (ESI+): 311 (M+1)$^+$, 309 (M−1)$^-$.

Separate the isomers using chiral chromatography (Chiralpak AD-H, 4.6×150 mm column, 10/90 3A/C7 w/0.2% dimethylethyl amine (DMEA eluent) to obtain the 4 separate isomers in 80-99% EE).

Example 22a

Isomer 1

98% EE, LCMS (APCI+): 100% @ 6.15 min, 311 (M+1)⁺.

Example 22b

Isomer 2

99% EE, LCMS (APCI+): 100% @ 6.16 min, 311 (M+1)⁺.

Example 22c

Isomer 3

95% EE, LCMS (APCI+): 100% @ 6.06 min, 311 (M+1)⁺.

Example 22d

Isomer 4

80% EE, LCMS (APCI+): 100% @ 6.06 min, 311 (M+1)⁺.

Preparation 24

N-(4-Bromo-3-chloro-2-methyl-phenyl)-acetamide

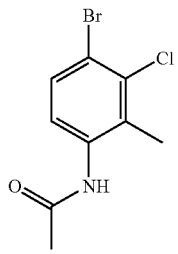

Dissolve N-(3-chloro-2-methyl-phenyl)-acetamide (120.0 g, 0.653 mol) in acetic acid and cool to 0° C. Add bromine (313.3 g, 1.96 mol) dropwise over 30 min via an addition funnel. Stir for 17 h while allowing the reaction to warm to room temperature. Pour the reaction into 1 L of ice, and filter. Rinse the filter cake with 4 L of water. The title product is isolated in 93.6% yield (160.6 g) as a white solid. MS: MS (ESI-): 262 (M-1)⁻. MS (ESI+): 263 (M+1)⁺.

Preparation 25

4-Amino-2-chloro-3-methyl-benzonitrile

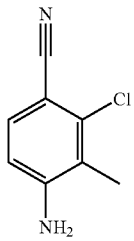

Dissolve N-(4-bromo-3-chloro-2-methyl-phenyl)-acetamide (10 g, 38 mmol) in N-methylpyrrolidinone (60 mL) and sparge with nitrogen. Add copper cyanide (10.2 g, 114 mol) and copper iodide (21.8 g, 114 mol) and stir under nitrogen at 130° C. for 72 h. Cool the reaction and add ethylene diamine (100 mL), along with water (300 mL). Extract the reaction mixture with EtOAc. Separate and dry the organic portion over Na₂SO₄, filter, and concentrate. Dissolve the resulting residue in 1:1 EtOH/concentrated HCl. Stir at reflux temperature for 30 min, cool and concentrate to half of the volume. Add water (500 mL) and filter. Rinse the filter cake with water and isolate 5.0 g (79%) of the title compound as a white solid. MS: MS (ESI-): 207 (M-1)⁻. MS (ESI+): 209 (M+1)⁺.

Example 23

2-Chloro-4-(2-ethyl-5-phenyl-pyrrolidin-1-yl)-3-methyl-benzonitrile

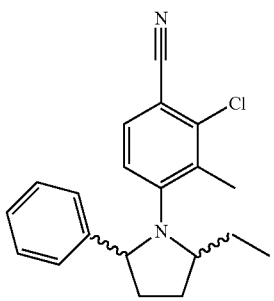

Dissolve methanesulfonic acid 4-methanesulfonyloxy-1-phenyl-hexyl ester (381 mg, 1.09 mmol) in toluene (10 mL) in a reaction tube. Add 4-amino-2-chloro-3-methylbenzonitrile (363 mg, 2.18 mmol), purge with nitrogen and cap. Heat the reaction in a 120° C. oil bath for 17 h. Cool, concentrate, and purify by silica gel chromatography using 5-30% EtOAc/hexanes to obtain 7 mg (1%) of the title compound (a mixture of 4 isomers) as a clear oil. MS (ESI+): 325 (M+1)⁺.

Instrumental Analysis

For Preparations 26-34 and Examples 24-31, below, the following analytical procedures are employed. Mass Spectrometric analysis is carried out on an Agilent 1100 Liquid Chromatography system attached to an Agilent G1946D Mass Selective Detector (MSD) using Atmospheric Pressure Electrospray Ionisation (API-ES or ESI). The Liquid Chromatograph employs a Supelco Discovery 100 mm×3 mm×5 um Reverse Phase LC column and uses an eluent flow rate of 1.0 ml/min. Eluants are: Solvent (A)—95% Acetonitrile:5% Water—with 0.04% (v/v) Formic Acid added or Solvent (B)—95% Water:5% Acetonitrile—with 0.04% (v/v) Formic Acid added. A solvent gradient is then employed—5% solvent A to 95% solvent A over a period of 7 minutes. Proton nuclear magnetic resonance (¹H NMR) spectra are collected on a Bruker DPX 300 MHz, Bruker DPX 400 MHz or Bruker DRX 500 MHz spectrometer. All products are a racemic mixture of R and S stereoisomers unless indicated otherwise.

Preparation 26

5-(1,3-benzodioxol-5-yl)-3,3-dimethyl-5-oxopentanoic acid

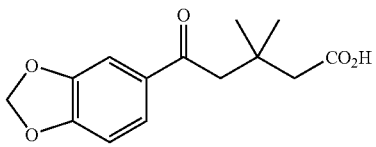

Cool a solution of 3,3-dimethylglutaric anhydride (5.16 g, 36.3 mmol) in tetrahydrofuran to about 0° C. using an ice water bath. Add 3,4-(methlyeneoxy)phenylmagnesium bromide (1M solution in tetrahydrofuran, 40 mL, 40.0 mmol) quickly under a flow of nitrogen gas. Stir for 30 min, then allow to warm to room temperature over a period of 1 h. Quench with saturated ammonium chloride solution. Dilute with water and ethyl acetate, separate the aqueous layer (pH=8-9) and then acidify using 1N HCl (pH=4-5). Extract using ethyl acetate, dry with magnesium sulfate, filter, and concentrate to afford the crude title compound as an orange/yellow oil (5.99 g). Subject the crude residue to flash chromatography (RediSep silica gel columns (120 g), gradient of 100:0 to 75:25 cyclohexane/ethyl acetate) to obtain 1.80 g (19%) of the title compound. $^1$H NMR (300 MHz, CDCl$_3$): δ 7.58-7.61 (m, 1H), 7.45 (s, 1H), 6.82-6.87 (m, 1H), 6.05 (s, 2H), 3.00 (s, 2H), 2.52 (s, 2H) and 1.15 (s, 6H).

Preparation 27

5-(1,3-benzodioxol-5-yl)-3,3-dimethyl-3,4-dihydro-2H-pyrrole

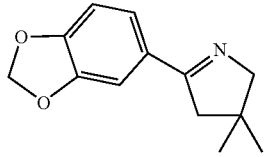

To a solution of 5-(1,3-benzodioxol-5-yl)-3,3-dimethyl-5-oxopentanoic acid (444 mg, 1.68 mmol) and N,N-diisopropylethylamine (0.292 mL, 1.68 mmol) in chloroform, add diphenylphosphorylazide (0.364 mL, 1.68 mmol). Stir at room temperature for 2 days, then treat with 2N NaOH. After 1 h, dilute the reaction with chloroform and water, then separate the organic layer and dry with magnesium sulfate, filter, and concentrate under reduced pressure to obtain 132 mg (36%) of the title compound. MS: 218 [M+H]$^+$; $^1$H NMR (300 MHz, CDCl$_3$): δ 7.40 (s, 1H), 7.20-7.24 (m, 1H), 6.78-6.81 (m, 1H), 6.00 (s, 2H), 3.75-3.74 (m, 2H), 2.72-2.71 (m, 2H) and 1.16 (s, 6H).

Preparation 28

2-(1,3-benzodioxol-5-yl)-4,4-dimethylpyrrolidine

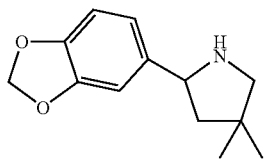

To a solution of 5-(1,3-benzodioxol-5-yl)-3,3-dimethyl-3,4-dihydro-2H-pyrrole (363 mg, 1.673 mmol) in acetonitrile (35 mL) add sodium triacetoxyborohydride (390 mg, 1.84 mmol) and stir at room temperature for two days. Then add more sodium triaxetoxyborohydride (390 mg, 1.84 mmol) and acetic acid and stir for 3 h. Add more add sodium triaxetoxyborohydride (390 mg, 1.84 mmol). After 0.5 h dissolve the reaction by adding methanol and load onto an ion-exchange SCX-2 (25 g), wash with methanol and then extract with ammonia in methanol. Concentrate under reduced pressure the basic solution, to afford 289 mg (79%) of the title compound. MS: 220 [M+H]$^+$; $^1$H NMR (300 MHz, CDCl$_3$): δ 6.90 (s, 1H), 6.72-6.75 (m, 1H), 6.72-6.75 (m, 1H), 5.91 (s, 2H), 4.20-4.25 (m, 1H), 2.68-2.72 (m, 1H), 2.75-2.79 (m, 1H), 1.72-1.98 (m, 2H), 1.45-1.1.53 (m, 1H), 1.10-1.18 (m, 6H).

Example 24

4-[2-(1,3-benzodioxol-5-yl)-4,4-dimethylpyrrolidin-1-yl]-2-chlorobenzonitrile

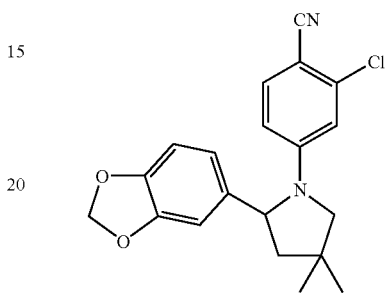

Combine 2-(1,3-benzodioxol-5-yl)-4,4-dimethylpyrrolidine (338 mg, 1.54 mmol) with 2-chloro-4-fluorobenzonitrile (216 mg, 1.39 mmol) and N-methylmorpholine (0.169 mL, 1.54 mmol) and then heat to 100° C. in a microwave for 1 h. Purify by flash chromatography (12 g RediSep silica gel columns, 0:100 to 90:10 gradient of [cyclohexane: ethylacetate] then repeat using (12 g RediSep silica gel columns, 0:100 to 97:3 gradient of [cyclohexane: ethylacetate] to provide 179 mg (36%) of the title compound. MS: 355 [M Cl$^{35}$+H]$^+$ and 377 [M Cl$^{35}$+Na]$^+$; $^1$H NMR (300 MHz, CDCl$_3$): δ 7.28-7.30 (m, 1H), 6.72-6.76 (m, 1H), 6.61-6.67 (m, 1H), 6.58 (s, 1H), 6.51 (s, 1H), 6.28-6.31 (m, 1H), 5.92-5.95 (m, 2H), 4.68-4.72 (m, 1H), 3.48-3.50 (m, 1H), 3.30-3.35 (m, 1H), 2.20-2.30 (1H, m), 1.75-1.81 (1H, m), 1.18 (s, 3H) and 1.09 (s, 3H).

Preparation 29

1-(3-chloro-4-cyano-2-methylphenyl)proline

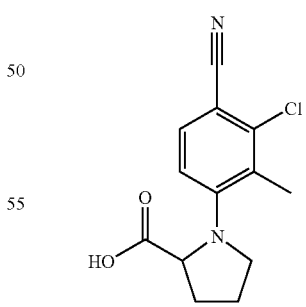

Heat a slurry of 2-chloro-4-fluoro-3-methyl-benzonitrile (0.4 g, 2.36 mmol) and L-proline (2.11 g, 18.8 mmol) in N-methylmorpholine (1.6 mL) at 200° C. in a microwave for 30 min. Partition the reaction between 2N aqueous hydrochloric acid and ethyl acetate. Separate and extract the organic portion with 2N aqueous sodium hydroxide. Acidify the aqueous extract to pH 1 by adding concentrated hydrochloric acid and back extract into ethyl acetate. Extract the combined organic portions with brine, dry over magnesium sulphate, filter, and concentrate under reduced pressure to give the title compound. (0.395 g, 63%) mass spectrum (m/e): 263 (M−1); $^1$H NMR (300 MHz, CDCl$_3$): δ 8.66 (bs, 1H0, 7.31 (d, 1H), 6.75 (d, 1H), 4.38 (t, 1H), 3.67 (m, 1H), 3.10 (m, 1H), 2.43 (m, 1H), 2.29 (s, 3H), 2.20-1.90 (m. 3H).

Preparation 30

N'-acetyl-2-[1-(3-chloro-4-cyano-2-methylphenyl) pyrrolidin-2-yl]acetohydrazide

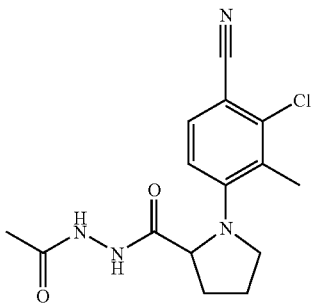

To a solution of 1-(3-chloro-4-cyano-2-methylphenyl)proline (0.600 g, 2.268 mmol), N,N-diisopropylethylamine (0.876 g, 6.816 mmol) and TBTU (1.092 g, 3.402 mmol) in DMF add a solution of acetic hydrazide (0.252 g, 3.402 mmols) in DMF. Leave to stand for 30 mins then partition between ethyl acetate and 2N aqueous hydrochloric acid. Extract the organic with 10% (w/w) aqueous sodium carbonate solution, then brine. Dry over magnesium sulphate, filter and concentrate under reduced pressure gives the title compound. (0.598 g, 82%) mass spectrum (m/e): 321 (M+H); $^1$H NMR (300 MHz, CDCl$_3$): δ 8.77 (s, 1H) 7.60 (bs, 1H) 7.40 (d, 1H), 6.88 (d, 1H), 4.35 (t, 1H), 3.86 (m, 1H), 3.04 (m, 1H), 2.51 (m, 1H), 2.44 (s, 3H), 2.00 (s, 3H), 2.22-1.85 (m. 3H).

Example 25

2-chloro-3-methyl-4-[2-(5-methyl-1,3,4-oxadiazol-2-yl)pyrrolidin-1-yl]benzonitrile

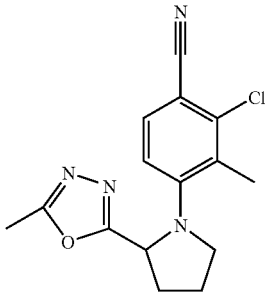

A mixture of N'-acetyl-2-[1-(3-chloro-4-cyano-2-methylphenyl)pyrrolidin-2-yl]acetohydrazide (0.400 g, 1.250 mmol), PS-BEMP (1.700 g, 3.750 mmol) and p-toluene sulphonyl chloride (0.285 g, 1.500 mmol) in THF is heated at reflux for 1.5 hours. The reaction is filtered, and the filtrate concentrated under reduced pressure. The residue is purified by reverse phase HPLC (Princeton SPHER C-18 column, gradient of 80:20 to 5:95 [water:acetonitrile], with 0.1% acetic acid modifier) to yield the title compound. (0.084 g, 22%) mass spectrum (m/e): 325.1 (M+Na); $^1$H NMR (400 MHz, CDCl$_3$): δ 7.38 (d, 1H), 6.99 (d, 1H), 5.10 (t, 1H), 3.86 (m, 1H), 3.14 (m, 1H), 2.51 (m, 1H), 2.43 (s, 3H), 2.38 (s, 3H), 2.35-1.93 (m. 3H).

Example 26

2-chloro-3-methyl-4-[2-(1,3,4-oxadiazol-2-yl)-1-pyrrolidinyl]benzonitrile

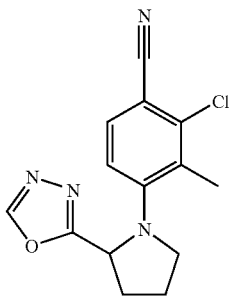

Prepare the title compound essentially as described in as Example 25. (0.008 g, 7.4%) mass spectrum (m/e): 289.0 (M+H); $^1$H NMR (400 MHz, CDCl$_3$): δ 8.23 (s, 1H), 7.36 (d, 1H), 6.95 (d, 1H), 5.22 (t, 1H), 3.84 (m, 1H), 3.16 (m, 1H), 2.56 (m, 1H), 2.39 (s, 3H), 2.35-1.98 (m. 3H).

Example 27

2-chloro-3-methyl-4-[2-(3-methyl-1,2,4-oxadiazol-5-yl)pyrrolidin-1-yl]benzonitrile

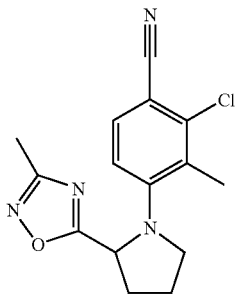

To a solution of 1-(3-chloro-4-cyano-2-methylphenyl)proline (0.200 g, 0.756 mmol), TBTU (0.364 g, 1.136 mmol), diisopropylethylamine (0.458 g, 3.78 mmol) and N-hydroxybenzotriazole (0.023 g, 0.150 mmol) in DMF add N-hydroxyacetamidine (0.084 g, 1.136 mmol). Stir the solution at 21° C. for 18 h. then heat the reaction at 100° C. in a microwave for 1 h. Partition the reaction between ethyl acetate and 2N aqueous hydrochloric acid. Extract the organic phase with 2N aqueous sodium hydroxide and brine, dry over magnesium sulphate, filter and remove the solvent under reduced pressure. Purify the resulting residue by reverse phase HPLC (Princeton SPHER C-18 column, gradient of 80:20 to 5:95 [water:acetonitrile], with 0.1% acetic acid modifier)) to yield the title compound. (0.81 g, 35%) mass spectrum (m/e): 303.1

(M+Na)); ¹H NMR (400 MHz, CDCl₃): δ 7.35 (d, 1H), 6.99 (d, 1H), 5.11 (t, 1H), 3.88 (m, 1H), 3.16 (m, 1H), 2.56 (m, 1H), 2.39 (s, 3H), 2.31 (s, 3H), 2.30-2.15 (m. 3H), 2.06 (m, 1H).

Example 28

2-chloro-3-methyl-4-[2-(5-methyl-1,3,4-thiadiazol-2-yl)pyrrolidin-1-yl]benzonitrile

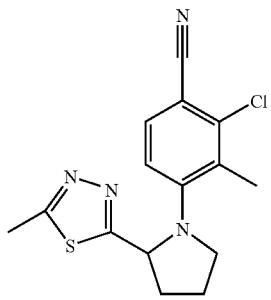

Heat a mixture of N-acetyl-2-[1-(3-chloro-4-cyano-2-methylphenyl)pyrrolidin-2-yl]acetohydrazide (0.200 g, 0.625 mmol) and Lawesson's reagent (0.505 g 1.250 mmol) in refluxing toluene for 3 h. Apply the reaction mixture to a silica SPE column (5 g, Isolute silica gel). Elute the column with cyclohexane, dichloromethane, chloroform and ethylacetate. Concentrate the ethyl acetate fraction and further purify the residue by flash chromatography (5 g, Isolute silica gel column, 50:1 [dichloromethane:methanol]). Further purify the residue containing the title compound by reverse phase HPLC (Princeton SPHER C-18 column, gradient of 80:20 to 5:95 [water:acetonitrile], with 0.1% acetic acid modifier) to yield the title compound. (0.063 g, 32%) mass spec (m/e): 319.0 (M+H); ¹H NMR (400 MHz, CDCl₃: δ 7.33 (d, 1H), 6.49 (d, 1H), 5.24 (t, 1H), 3.94 (m, 1H), 3.05 (m, 1H), 2.58 (m, 1H), 2.56 (s, 3H), 2.42 (s, 3H), 2.25-2.08 (m. 3H).

Preparation 30 tert-butyl 2-{[1-(3-chloro-4-cyano-2-methylphenyl)pyrrolidin-2yl]acetyl}hydrazinecarboxylate

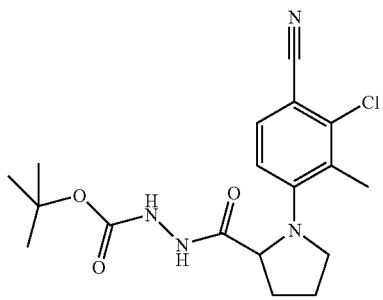

To a solution of 1-(3-chloro-4-cyano-2-methylphenyl)proline (0.623 g, 2.350 mmol), N,N-diisopropylethylamine (1.420 g, 11.750 mmol) and TBTU (1.113 g, 3.530 mmol) in DMF add a solution of t-butlycarbazate (0.462 g, 3.530 mmols) in DMF. Leave to stand for 3 h, then partition between ethyl acetate and 10% (w/w) aqueous citric acid. Extract the organic with 2N aqueous sodium hydroxide solution, then brine. Dry over magnesium sulphate, filter, and concentrate under reduced pressure to obtain the title compound. (0.89 g, 100%) mass spectrum (m/e): 379 (M+H); ¹H NMR (300 MHz, CDCl₃): δ 7.80 (s, 1H), 7.42 (d, 1H), 6.38 (d, 1H), 6.22 (bs, 1H) 4.33 (t, 1H), 3.88 (m, 1H), 3.04 (m, 1H), 2.81 (m, 3H), 2.53 (m, 1H), 1.85-2.38 (m. 3H), 1.41 (s, 9H).

Preparation 31

2-[1-(3-chloro-4-cyano-2-methylphenyl)pyrrolidin-2-yl]acetohydrazide

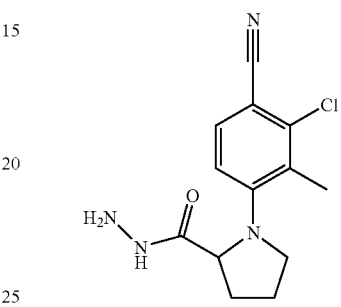

Mix a solution of tert-butyl 2-{[1-(3-chloro-4-cyano-2-methylphenyl)pyrrolidin-2-yl]acetyl}hydrazinecarboxylate (0.897 g, 2.35 mmol) in trifluoroacetic acid at ambient temperature for 30 min. Remove the solvent under reduced pressure, dissolve the residue into methanol and apply to a cationic exchange column (10 g Isolute SCX-2). Elute the column with methanol then 2N methanolic ammonia. Concentrate the methanolic ammonia fractions under reduced pressure to obtain the title compound. (0.577 g, 88%) mass spectrum (m/e): 279.1 (M+H); ¹H NMR (300 MHz, CDCl₃): δ 7.41 (d, 1H), 6.82 (d, 1H), 7.30 (bs, 1H), 4.28 (t, 1H), 3.82 (m, 1H) 3.73 (s. 2H), 3.00 (m, 1H), 2.54 (m, 1H), 2.56 (s, 3H), 2.40 (s, 3H), 1.80-2.10 (m. 3H).

Example 29

2-chloro-3-methyl-4-[2-(5-methyl-4H-1,2,4-triazol-3-yl)pyrrolidin-1-yl]benzonitrile

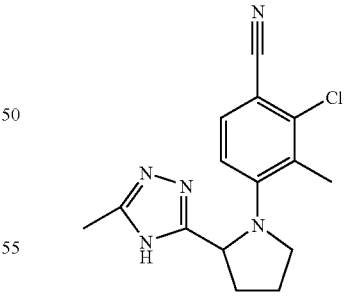

Heat a solution of 2-[1-(3-chloro-4-cyano-2-methylphenyl)pyrrolidin-2-yl]acetohydrazide (0.200 g, 0.719 mmol) and ethyl acetimidate hydrochloride (0.133 g, 1.078 mmol) in triethylamine and isopropyl alcohol at 85° C. for 3 h, then at reflux for 2 h. Add more ethyl acetimidate hydrochloride (0.133 g, 1.078 mmol) and reflux for 2 h. Concentrate the reaction under reduced pressure and partition the residue between ethyl acetate and water. Extract the organic layer with brine, dry over magnesium sulphate, and concentrate under reduced pressure. Purify the residue by reverse phase HPLC (Princeton SPHER C-18 column, gradient of 80:20 to 5:95 [water:acetonitrile], with 0.1% acetic acid modifier) to yield the title compound. (0.074 g, 34%) mass spectrum (m/e): 302.1 (M+H); $^1$H NMR (400 MHz, CDCl$_3$): δ 7.28 (d, 1H), 6.90 (d, 1H), 4.95 (t, 1H), 3.94 (m, 1H), 3.12 (m, 1H), 2.50 (m, 1H), 2.34 (s, 3H), 2.31 (s, 3H), 1.88-2.28 (m. 3H).

Preparation 32

N'-carbamoyl-2-[1-(3-chloro-4-cyano-2-methylphenyl)pyrrolidin-2-yl]acetohydrazide

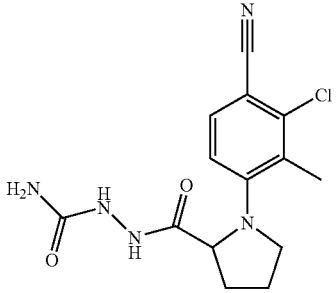

To a solution of 2-[1-(3-chloro-4-cyano-2-methylphenyl)pyrrolidin-2-yl]acetohydrazide (0.288 g, 1.030 mmol) in dichloromethane and diisopropylethylamine, add trimethylsilyl isocyanate (0.238 g, 2.060 mmol) and stir the reaction at 21° C. for 2 h. Partition the reaction is between ethyl acetate and brine. Dry the organic phase over magnesium sulphate, filter, and remove the solvent is under reduced pressure to yield the title compound. (0.303 g, 91%) mass spectrum (m/e): 322.1 (M+H); $^1$H NMR (300 MHz, CDCl$_3$): δ 8.37 (s, 1H) 7.38 (d, 1H), 7.30 (s, 1H), 6.34 (d, 1H), 5.04 (s, 2H), 4.34 (t, 1H), 3.86 (m, 1H), 3.08 (m, 1H), 2.46 (m, 1H), 2.42 (s, 3H), 2.03 (s, 3H), 2.20-1.85 (m. 3H).

Example 30

4-[2-(5-amino-1,3,4-oxadiazol-2-yl)pyrrolidin-1-yl]-2-chloro-3-methylbenzonitrile

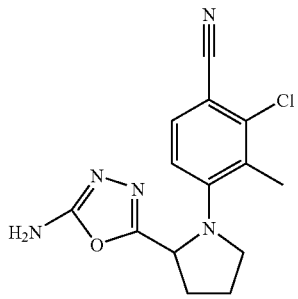

Heat a mixture of N'-carbamoyl-2-[1-(3-chloro-4-cyano-2-methylphenyl)pyrrolidin-2-yl]acetohydrazide (0.300 g, 0.933 mmol), P-BEMP (1.27 g, 2.798 mmol), p-toluenesulphonyl chloride (0.212 g, 1.119 mmol) at reflux for 2 h. Filter the reaction and concentrate the filtrate under reduced pressure. Purify the residue by reverse phase HPLC (Princeton SPHER C-18 column, gradient of 80:20 to 5:95 [water:acetonitrile], with 0.1% acetic acid modifier) to yield the title compound. (0.024 g, 8.4%) mass spectrum (m/e): 304.1 (M+H); $^1$H NMR (400 MHz, CDCl$_3$): δ 7.37 (d, 1H), 6.95 (d, 1H), 4.98 (t, 1H), 4.85 (bs, 2H), 3.79 (m, 1H), 3.10 (m, 1H), 2.45 (m, 1H), 2.39 (s, 3H), 2.38-1.90 (m. 3H).

Preparation 33

4-Hydroxy-4-phenyl-butene-1,2-oxide

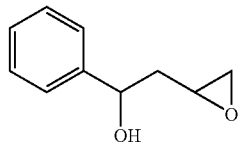

Stir a solution of 4-hydroxy-4-phenyl-1-butene (ex Aldrich, 3.5 g, 23 mmol) and meta-chloro-peroxybenzoic acid (60% w/w, 7.0 g, 24 mmol) in dichloromethane 18 h at room temperature and wash with 10% aqueous sodium hydrogen sulphite (100 ml) followed by 1.0M aqueous sodium hydroxide (100 ml). Dry the organic layer over magnesium sulphate, filter and concentrate to obtain 3.6 g (95% yield of a 1:1 mixture of diastereoisomers) of the title compound as a colourless oil. $^1$H NMR (300 MHz, CDCl$_3$): 7.30 (m, 5H), 4.95 (m, 1H), 3.16 and 2.98 (m, 1H), 2.81 and 2.73 (m, 1H), 2.60 and 2.49 (m, 1H), 2.10 (m, 1H), 1.88 (m, 1H).

Preparation 34

2,4-Dihydroxy-4-phenyl-1-butylamine

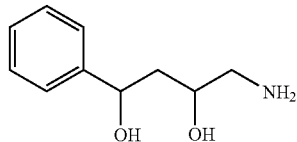

Add a 7.0M solution of ammonia in methanol (20 ml) to 4-hydroxy-4-phenyl-butene-1,2-oxide (3.6 g, 22 mmol) and allow the reaction to stand at room temperature for 24 h. Concentrate the mixture to dryness, dissolve in 10 ml methanol and transfer to a 50 g SCX-2 cartridge. Elute the cartridge with methanol (200 ml) and then with 2.0M ammonia in methanol (200 ml). Concentrate the ammonia fraction to obtain 3.3 g (83%) of the title compound as a pale yellow solid. $^1$H NMR (300 MHz, MeOD): δ 7.30 (m, 5H), 4.90 (m, 1H), 3.95 and 3.68 (m, 1H), 3.82-2.65 (m, 2H), 2.00-1.73 (m, 2H).

Example 31

2-Chloro-3-methyl-4-(4-hydroxy-2-phenyl-pyrrolidin-1-yl)-benzonitrile

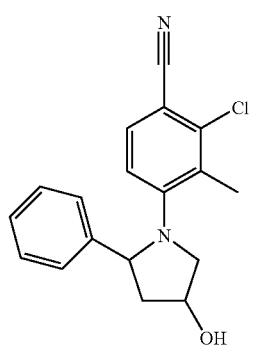

Heat a mixture of 2,4-dihydroxy-4-phenyl-1-butylamine (1.8 g, 10 mmol) and 2-chloro-4-fluoro-3-methyl-benzonitrile (1.0 g 6 mmol), cesium carbonate (4.0 g, 12 mmol) and anhydrous dimethyl sulphoxide (10 ml) at 100° C. for 5 h. Allow the reaction cool and partition between ethyl acetate (100 ml) and water (3×50 ml). Wash the organic layer with 1.0M hydrochloric acid, dry over magnesium sulphate and concentrate to give a yellow oil (1.0 g). Dissolve this material in dichloromethane (20 ml) and treat with trifluoroacetic acid (5 ml). Allow the reaction mixture to stand at room temperature overnight and then wash with water (20 ml) and 2.0M sodium hydroxide (20 ml). Dry the organic layer over magnesium sulphate and concentrate to dryness. Purify the residue by silica gel chromatography (eluting with 5 to 10% methanol/dichloromethane) to give 50 mg (1.6% yield as a single diastereoisomer) of the title compound as a white solid. MS: 313 [M Cl$^{35}$+H]$^+$ and 335 [M Cl$^{35}$+Na]$^+$; $^1$H NMR (300 MHz, CDCl$_3$): δ 7.28 (m, 5H), 7.20 (d, 1H), 6.72 (d, 1H), 5.09 (m, 1H), 4.60 (br m, 1H), 4.29 (m, 1H), 3.10 (m, 1H), 2.44 (m, 1H), 2.43 (s, 3H), 2.00 (m, 1H).

Preparation 35

N-methoxy-N-methylnicotinamide

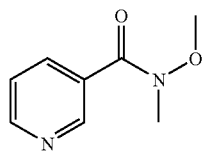

Add triethylamine (11.9 mL, 84.5 mmol) dropwise to a suspension of nicotinic acid (10 g, 81.2 mmol), N,O-dimethylhydroxylamine hydrochloride (8.3 g, 85.3 mmol, 1.05 eq), 1-hydroxybenzotriazole (3.29 g, 24.36 mmol, 0.3 eq) and 1,3-dimethylamino propyl-3-ethylcarbodiimide hydrochloride (18.68 g, 97.44 mmol, 1.2 eq) in acetonitrile (100 mL) at room temperature under nitrogen. After 2 h a white precipitate forms. Add water (100 mL) and acetonitrile and evaporate under vacuum. Extract with ethyl acetate (3×100 mL), dry the organic phase over anhydrous sodium sulfate and concentrate to afford 13.19 g (98%) of the title compound.

Preparation 36

3-Methyl-1-pyridin-3-yl-but-2-en-1-one

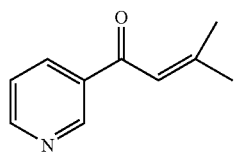

To a solution of N-methoxy-N-methylnicotinamide (500 mg, 3.0 mmol) in anhydrous THF (3.5 mL) under nitrogen at −78° C. add 2-methyl propenyl magnesium bromide (12 mL, 6.0 mmol, 0.5 M in THF) dropwise. After one hour at −78° C., allow to reach room temperature. After 2 h, add saturated aqueous ammonium chloride. (10 mL) and water (2 mL). Extract with ethyl acetate three times, dry the combined organic phases with anhydrous sodium sulfate and concentrate to obtain 442 mg (91%) of the title compound as a yellow oil.

Preparation 37

3,3-Dimethyl-4-nitro-1-pyridin-3-yl-butan-1-one

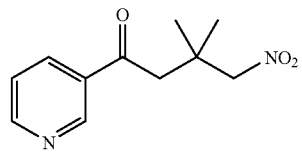

To a mixture of 3-methyl-1-pyridin-3-yl-but-2-en-1-one (440 mg, 2.73 mmol) and nitromethane (0.74 mL, 13.65 mmol) that is cooled with a water bath, add DBU (0.41 mL, 2.73 mmol) dropwise. After 30 min, add ether (15 mL) and 1N hydrochloric acid (15 mL). Neutralize with 1M NaOH and extract with ether. Dry over magnesium sulfate and evaporate to obtain 340 mg (61%) of the title compound as a yellow solid.

Preparation 38

4-Methyl-5-nitro-2-pyridin-3-yl-pentan-2-ol

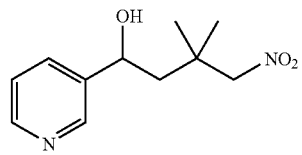

To a solution of 3,3-dimethyl-4-nitro-1-pyridin-3-yl-butan-1-one (1 g, 4.5 mmol) in methanol (6 mL) under nitrogen add sodium borohydride (684 mg, 18 mmol). Stir at room temperature for 2 h, evaporate the methanol, dissolve in ethyl acetate and wash with water. Dry the organic layer over anhydrous sodium sulfate and concentrate to obtain 860 mg (85%) of the title compound.

Preparation 39

5-Amino-4-methyl-2-pyridin-3-yl-pentan-2-ol

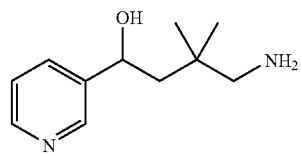

Stir a mixture of 4-methyl-5-nitro-2-pyridin-3-yl-pentan-2-ol (860 mg, 3.84 mmol) and Pt—C(S) (200 mg) in EtOH (25 mL) at room temperature under hydrogen atmosphere (7 atm) for 24 h. Filter through a pad of Celite® and evaporate to obtain 630 mg (84%) of the title compound.

Preparation 40

2-Chloro-4-(4-hydroxy-2,2-dimethyl-4-pyridin-3-yl-butylamino)-3-methyl-benzonitrile

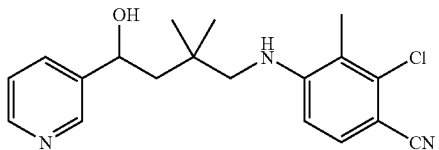

Heat a solution of 5-amino-4-methyl-2-pyridin-3-yl-pentan-2-ol (630 mg, 3.24 mmol) and 2-chloro-4-fluoro-3-methyl-benzonitrile (493 mg, 2.92 mmol) in NMP (2 mL) at 120° C. for 2 h in a microwave reactor. Purify the crude product by SCX to obtain 570 mg (51%) of the title compound.

Example 32

2-Chloro-4-(4,4-dimethyl-2-pyridin-3-yl-pyrrolidin-1-yl)-3-methyl-benzonitrile

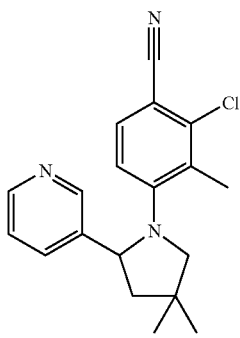

To a solution of 2-chloro-4-(4-hydroxy-2,2-dimethyl-4-pyridin-3-yl-butylamino)-3-methyl-benzonitrile (570 mg, 1.66 mmol) in pyridine (2.3 mL) add tosyl chloride (950 mg, 4.98 mmol) in pyridine (1.2 mL) at room temperature. Heat the reaction mixture at 100° C. for 24 h, add additional tosyl chloride (950 mg), and heat for 24 h at 100° C. Cool to room temperature and concentrate under vacuum. Dissolve the residue in ethyl acetate and wash with water. Dry the organic layer over anhydrous sodium sulfate and concentrate to obtain a brown oil. Purify the oil by silica gel chromatography and preparative HPLC to obtain the title compound. Mass spectrum (m/e): 326 (M+H).

Biological Data

TABLE I

| Ex. | AR binding Ki (nM) | C2C12 EC50(nM) | C2C12 % Efficacy | (n) |
|---|---|---|---|---|
| 1 | 1.4 | 1.2 | 67.6 | 3 |
| 2 | 4.3 | 36.7 | 61.0 | 2 |
| 3 | 2.7 | 5.1 | 51.1 | 3 |
| 4 | 6.6 | 11.2 | 84.9 | 3 |
| 5 | 1.1 | 0.9 | 102.3 | 2 |
| 6 | 7.0 | 177.0 | 81.7 | 2 |
| 7 | 3.4 | 28.3 | 68.9 | 4 |
| 8 | 72.9 | nd | −38.5 | 2 |
| 9 | 1.3 | 2.6 | 90.7 | 6 |
| 10 | 4.7 | 40.8 | 79.8 | 4 |
| 11 | 6.0 | 6.8 | 76.8 | 6 |
| 12 | 2.2 | 12.4 | 95.6 | 2 |
| 13 | 5.8 | 9.7 | 84.7 | 6 |
| 14 | 13.4 | 21.2 | 73.1 | 6 |
| 15 | 2.8 | 0.4 | 85.1 | 2 |
| 16 | 17.4 | 108.9 | 42.6 | 2 |
| 17 | 27.3 | nd | 13.2 | 2 |
| 18 | 24.4 | 9.8 | 77.9 | 2 |
| 19 | 17.6 | nd | −12.4 | 4 |
| 20 | 21.1 | 516.1 | 4.8 | 1 |
| 21 | 3.0 | 103.4 | 58.1 | 4 |
| 22 | 4.9 | 17.7 | 85.5 | 3 |
| 22a | 121.9 | 32.4 | 92.4 | 2 |
| 22b | 39.9 | 25.0 | 80.6 | 2 |
| 22c | 39.8 | 135.0 | 61.3 | 3 |
| 22d | 2.2 | 6.1 | 66.5 | 2 |
| 23 | 27.1 | 130.9 | 70.1 | 1 |
| 24 | 12.7 | 397.0 | 23.4 | 3 |
| 25 | 3.7 | 0.9 | 80.5 | 5 |
| 26 | 5.4 | 4.2 | 82.7 | 3 |
| 27 | 1.9 | 0.5 | 87.6 | 4 |
| 28 | 9.0 | 24.4 | 74.3 | 3 |
| 29 | 58.9 | 377.8 | 83.9 | 4 |
| 30 | 18.7 | 37.9 | 95.7 | 4 |
| 31 | 8.3 | 20.7 | 91.6 | 4 |

"Ex" = Example Number
"nd" = not determined

In Vivo Data of Select Examples:

TABLE II

| Example | Dose (mg/kg/d), route | % Efficacy: (ANOVA, p < 0.05) |
|---|---|---|
| 9 | 10, sc | 186% |
| 12 | 10, po | 164% |

Seminal vesicle and/or prostate showed no weight gain with Examples 9 and 12.

We claim:

1. A compound of the formula:

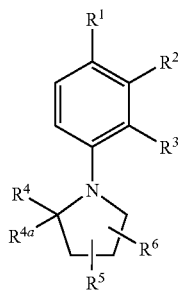

Formula I wherein,
- $R^1$ represents CN;
- $R^2$ represents halo, halo($C_1$-$C_4$)alkyl, or ($C_1$-$C_4$)alkyl;
- $R^3$ represents H or ($C_1$-$C_4$)alkyl;
- $R^4$ represents a phenyl group optionally substituted with a substituent selected from the group consisting of halo, methyl, ethyl, methoxy, ethoxy, $CF_3$, $CHF_2$, $OCF_3$, —$SR^7$, or —$SO_2R^8$;
- $R^{4a}$ represents hydrogen or methyl;
- $R^5$ represents H, OH, $CH_2OH$, halo, or ($C_1$-$C_4$)alkyl;
- $R^6$ represents H, OH, or ($C_1$-$C_4$)alkyl, provided that when $R^5$ and $R^6$ each represent OH, they are not bound to the same carbon atom; and
- $R^7$ and $R^8$ each independently represent at each occurrence ($C_1$-$C_4$)alkyl, or a pharmaceutically acceptable salt thereof.

2. The compound or salt according to claim 1 wherein R2 represents fluoro, chloro, bromo, halo($C_1$-$C_4$)alkyl, or methyl.

3. The compound or salt according to claim 2 wherein R2 represents chloro or trifluoromethyl.

4. The compound or salt according to claim 1 wherein R3 represents hydrogen, methyl, ethyl, propyl, isopropyl, isobutyl, or tert-butyl.

5. The compound or salt according to claim 4 wherein R3 represents hydrogen, methyl, or ethyl.

6. The compound or salt according to claim 5 wherein R3 represents hydrogen or methyl.

7. The compound or salt according to claim 1 wherein $R^4$ represents a phenyl group optionally substituted with a substituent selected from the group consisting of fluoro, chloro, methoxy, $CF_3$, SMe, or $SO_2Me$.

8. The compound or salt according to claim 7 wherein R4 represents a group of the formula:

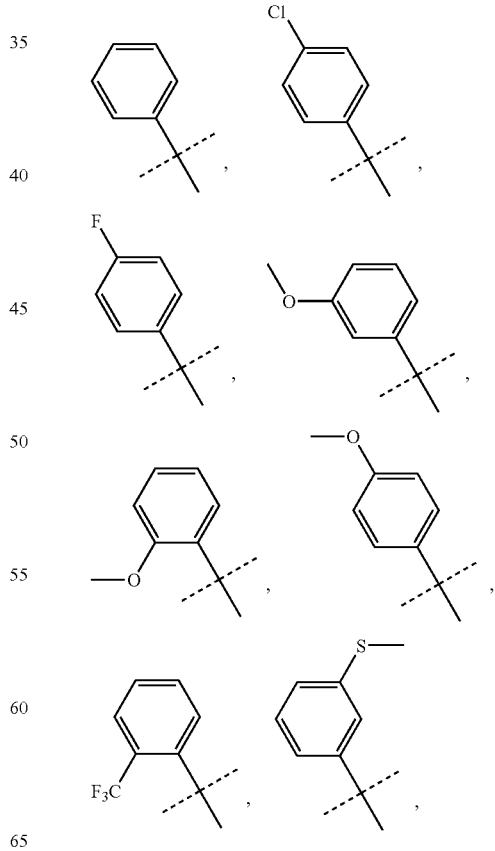

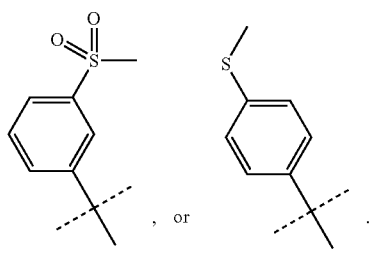, or

9. The compound or salt according to claim 1 wherein R5 represents hydrogen, halo, hydroxy, or $(C_1$-$C_4)$alkyl.

10. The compound or salt according to claim 9 wherein R5 represents hydrogen, hydroxy, or methyl.

11. The compound or salt according to claim 10 wherein R5 represents hydrogen or methyl.

12. The compound or salt according to claim 1 wherein R6 represents hydrogen or $(C_1$-$C_4)$alkyl.

13. The compound or salt according to claim 12 wherein R6 represents hydrogen or methyl.

14. A compound according to claim 1 selected from the group consisting of:

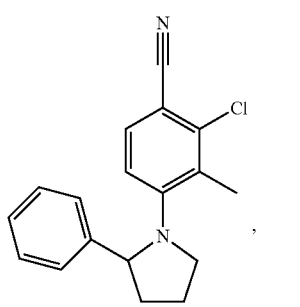,

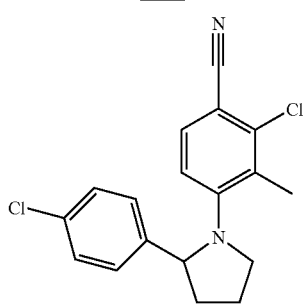,

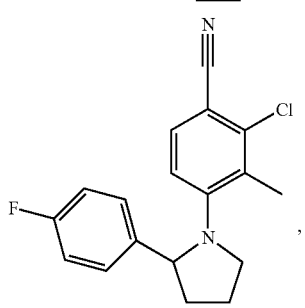,

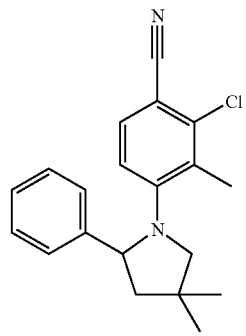,

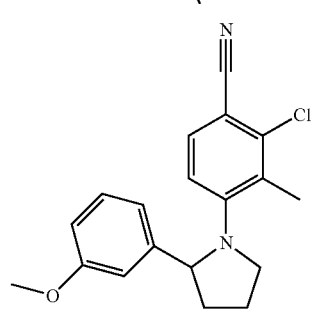,

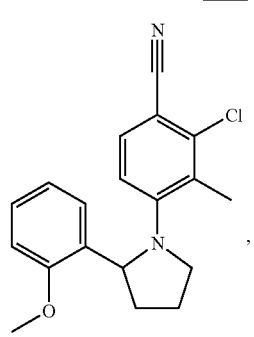,

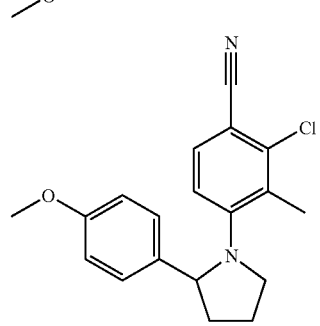,

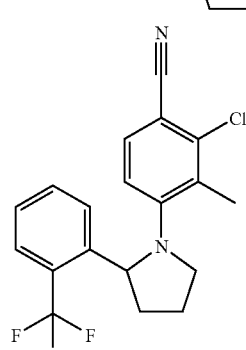,

-continued
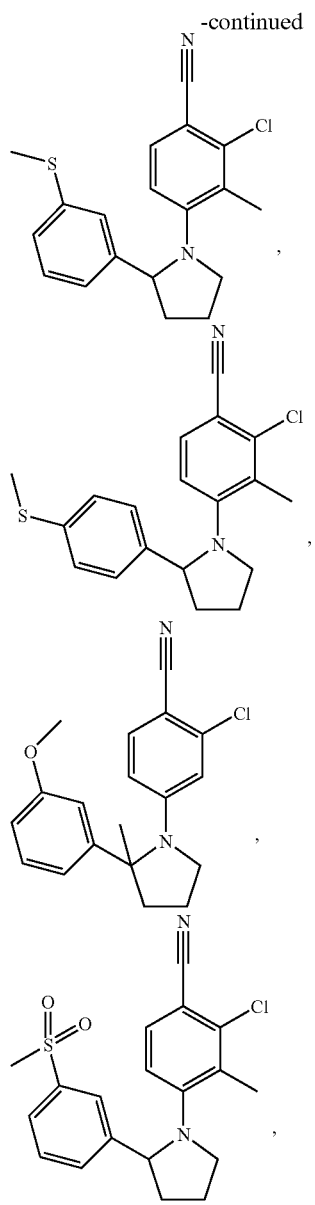
-continued
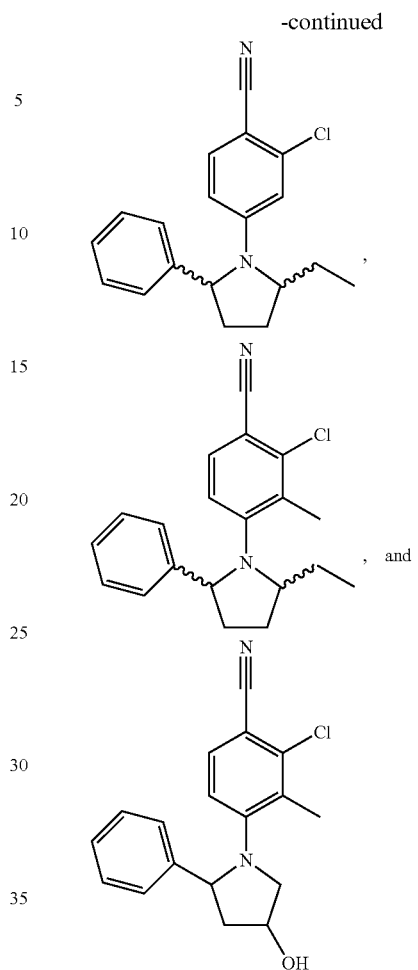
or a pharmaceutically acceptable salt thereof.
15. A pharmaceutical composition comprising as an active ingredient a compound or salt according to claim 1 in combination with a pharmaceutically acceptable carrier, diluent or excipient.
* * * * *